United States Patent
Vetro

(10) Patent No.: US 9,320,814 B2
(45) Date of Patent: Apr. 26, 2016

(54) POLYPLEXES OF HYDROPHOBICALLY-MODIFIED SIRNA FOR DELIVERY OF SIRNA

(71) Applicant: Board of Regents of the University of Nebraska, Lincoln, NE (US)

(72) Inventor: Joseph A. Vetro, Logan, IA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/666,021

(22) Filed: Nov. 1, 2012

(65) Prior Publication Data

US 2013/0123336 A1 May 16, 2013

Related U.S. Application Data

(60) Provisional application No. 61/554,101, filed on Nov. 1, 2011.

(51) Int. Cl.
  *C12N 15/11* (2006.01)
  *A61K 48/00* (2006.01)
  *A61K 45/06* (2006.01)

(52) U.S. Cl.
  CPC ............ *A61K 48/0041* (2013.01); *A61K 45/06* (2013.01)

(58) Field of Classification Search
  CPC ............ A61K 48/0041; C12N 15/113; C07K 14/4702
  See application file for complete search history.

(56) References Cited

U.S. PATENT DOCUMENTS

| | | | |
|---|---|---|---|
| 2006/0025330 A1 * | 2/2006 | Sakurai et al. | 514/2 |
| 2009/0053169 A1 * | 2/2009 | Castillo et al. | 424/85.2 |
| 2010/0130588 A1 * | 5/2010 | Yaworski et al. | 514/44 A |

FOREIGN PATENT DOCUMENTS

WO  WO 9615778 A1 *  5/1996

OTHER PUBLICATIONS

Healy et al, Pharmacokinetics and Biodistribution of Novel Aptamer Compositions, 2004, Pharmaceutical Research, vol. 21, No. 12, pp. 2234-2246.*
Kano, A., et al. "Grafting of poly(ethylene glycol) to poly-lysine augments its lifetime in blood circulation and accumulation in tumors without loss of the ability to associate with siRNA." J Control Release. Jan. 5, 2011;149(1):2-7. Epub Dec. 21, 2009.
Oba, M., et al. "Polyplex micelles prepared from w-cholesteryl PEG-polycation block copolymers for systemic gene delivery." Biomaterials. Jan. 2011;32(2):652-63. Epub Oct. 6, 2010.
Christie, R.J., et al. "Delivering the code: polyplex carriers for deoxyribonucleic acid and ribonucleic acid interference therapies." Endocrinology. Feb. 2010;151(2):466-73. Epub Dec. 23, 2009.
Ambardekar, V.V., et al. "The modification of siRNA with 3' cholesterol to increase nuclease protection and suppression of native mRNA by select siRNA polyplexes." Biomaterials. Feb. 2011;32(5):1404-11. Epub Nov. 2, 2010.

* cited by examiner

*Primary Examiner* — Tracy Vivlemore
*Assistant Examiner* — Kate Poliakova-Georgantas
(74) *Attorney, Agent, or Firm* — Robert C. Netter, Jr.; Dann, Dorfman, Herrell & Skillman

(57) ABSTRACT

The present invention provides compositions and methods for delivering nucleic acid molecules to a cell.

15 Claims, 12 Drawing Sheets

Figure 1:
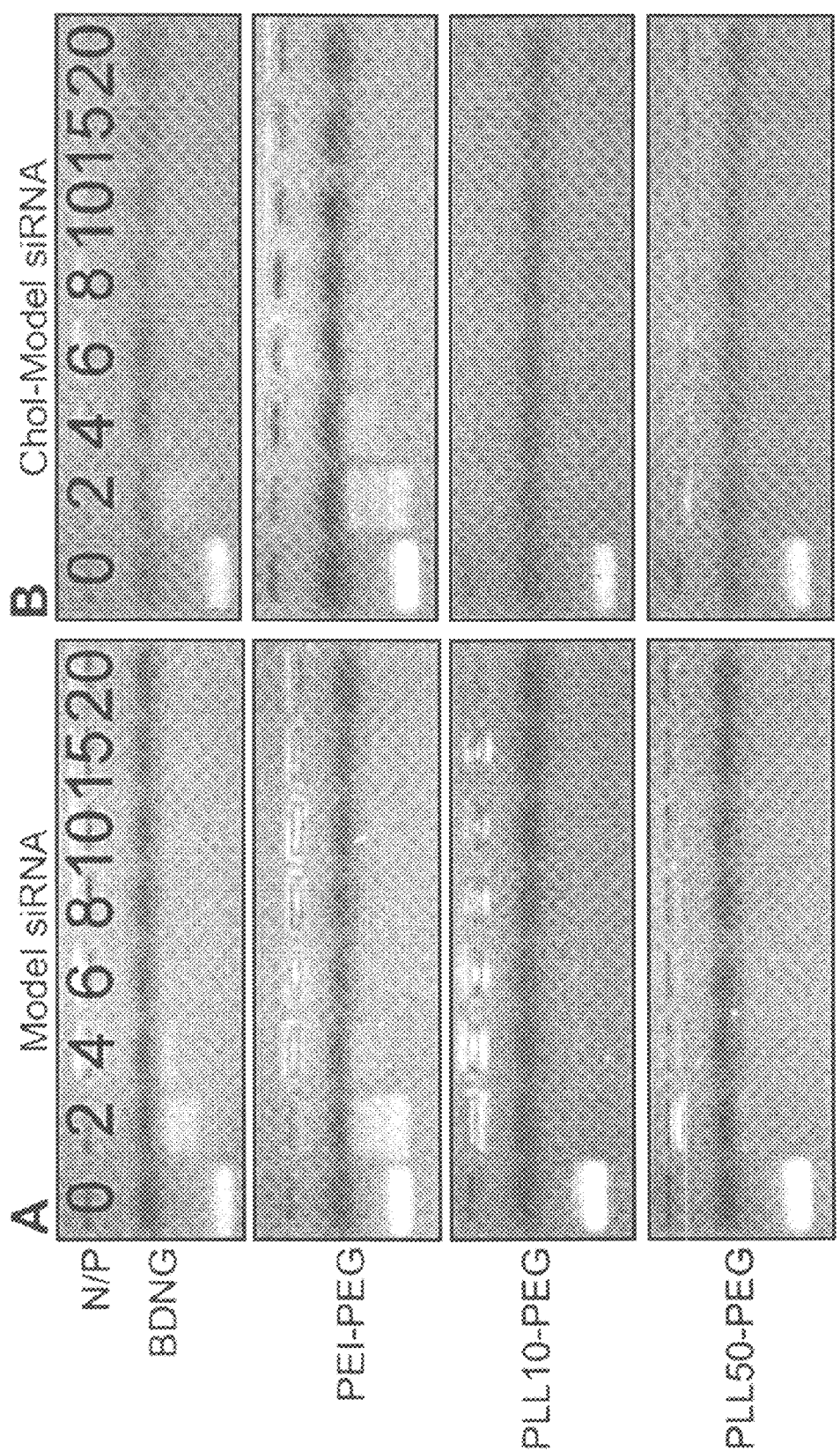

PLL30-PEG-chol-*siCtrl    PLL30-PEG-chol-*siLuc d0      d2                 d0      d2

PLL50-PEG-chol-*siCtrl    PLL50-PEG-chol-*siLuc d0      d2                 d0      d2

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1
ctcgatagaa tacacaggca t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic sequence

<400> SEQUENCE: 2
gcctgtgtat tctatcgaga t                                            21

<210> SEQ ID NO 3
<211> LENGTH: 19
<212> TYPE: RNA
```

```
<213> ORGANISM: Artificial Sequence
<220> FEATURE:
<223> OTHER INFORMATION: Synthetic sequence

<400> SEQUENCE: 3
caaguuccau cgugucauc                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic sequence

<400> SEQUENCE: 4
caaguuccau cgugucauc                                                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic sequence

<400> SEQUENCE: 5
cggcaaaguu cuagagggc                                                    19

<210> SEQ ID NO 6
<211> LENGTH: 19
<212> TYPE: RNA
<213> ORGANISM: Artificial Sequence
<220> FEATURE:
<223> OTHER INFORMATION: Synthetic sequence

<400> SEQUENCE: 6
ggagaaaccc uucgccauu                                                    19

<210> SEQ ID NO 7
<211> LENGTH: 19
<212> TYPE: RNA
<213> ORGANISM: Artificial Sequence
<220> FEATURE:
<223> OTHER INFORMATION: Synthetic sequence

<400> SEQUENCE: 7
gaaagagcau cuaugguga                                                    19

<210> SEQ ID NO 8
<211> LENGTH: 19
<212> TYPE: RNA
<213> ORGANISM: Artificial Sequence
<220> FEATURE:
<223> OTHER INFORMATION: Synthetic sequence

<400> SEQUENCE: 8
ugguuuacau gucgacuaa                                                    19
```

POLYPLEXES OF HYDROPHOBICALLY-MODIFIED SIRNA FOR DELIVERY OF SIRNA

This application claims priority under 35 U.S.C. §119(e) to U.S. Provisional Patent Application No. 61/554,101, filed Nov. 1, 2011. The foregoing application is incorporated by reference herein.

This invention was made with government support under Grant Nos. 5 R21 EB005683-02 and P20 GM103480 awarded by the National Institutes of Health. The government has certain rights in the invention.

FIELD OF THE INVENTION

The present invention relates generally to compositions and methods for delivering a nucleic acid molecule to a cell.

BACKGROUND OF THE INVENTION

Several publications and patent documents are cited throughout the specification in order to describe the state of the art to which this invention pertains. Each of these citations is incorporated herein by reference as though set forth in full.

Small interfering RNA (siRNA) is a naturally occurring dsRNA molecule, typically 21-23 nucleotides, processed from longer dsRNA (Bernstein et al. (2001) Nature 409:363-6) that selectively and persistently suppresses the expression of proteins through the catalytic, sequence-specific degradation of mRNA (Elbashir et al. (2001) Nature 411:494-8). As such, siRNA has tremendous potential in therapeutic applications where the suppression or absence of a protein or multiple proteins can produce a clinically beneficial result. Furthermore, many proteins identified as drug targets that cannot be inhibited by conventional low molecular weight drug candidates can potentially be inhibited by siRNA (Shen, Y. (2008) IDrugs 11:572-8).

siRNA can be administered directly as synthetic siRNA (typically 19 bp dsRNA with two 3' nucleotide overhangs on each strand) that functions upon entry into the cytosol (Elbashir et al. (2001) Nature 411:494-8) or as pDNA that functions after entry into the nucleus and subsequent expression of short hairpin loops of RNA (shRNA) for cytosolic processing into siRNA (Brummelkamp et al. (2002) Science 296:550-3). siRNA is incorporated into an RNA-induced silencing complex (RISC) within the cytosol (Rand et al. (2004) Proc. Natl. Acad. Sci., 101:14385-9) where the sense strand is degraded to reveal the antisense strand (Matranga et al. (2005) Cell 123:607-20) and form an activated RISC. Activated RISC then facilitates the degradation of mRNA that is complementary to the loaded antisense strand (Ameres et al. (2007) Cell 130:101-12) and remains active (Hutvagner et al. (2002) Science 297:2056-60) for 3-7 days in dividing cells and for several weeks in non-dividing cells (Bartlett et al. (2006) Nucleic Acids Res., 34:322-33).

Although pDNA has the potential to deliver higher and more sustained dosages of siRNA, unpredictable and subsequently toxic dosages in vivo have been reported (Grimm et al. (2006) Nature 441:537-41). Furthermore, synthetic siRNA, unlike pDNA, does not need to enter and rely on the host nucleus for subsequent function. Thus, from a pharmaceutical perspective, synthetic siRNA is likely safer because dose can be tightly controlled and potentially more effective due to fewer intracellular barriers. Many clinical applications require the systemic administration of siRNA to achieve a therapeutic effect. The systemic administration of siRNA, however, is limited by several obstacles, including: (i) the extremely short plasma half-life of siRNA due to degradation by nuclease activity and renal clearance; (ii) low level cellular uptake of siRNA due to its large size (13 kDa) and negative charge; and (iii) the inability of siRNA to escape the endosomes/lysosomes into the cytosol, the site of activity (Whitehead et al. (2009) Nat. Rev. Drug. Discov., 8:129-38; Aigner, A. (2008) Curr. Pharm. Des., 14:3603-19; Howard, K. A. (2009) Adv. Drug Deliv. Rev., 61:710-20).

Polymer-siRNA complexes (siRNA polyplexes) are being actively developed to improve the systemic administration of siRNA (Aigner, A. (2008) Curr. Pharm. Des., 14:3603-19). The design of siRNA polyplexes requires balancing many requirements including: (i) protecting siRNA molecules against nuclease degradation in the plasma; (ii) increasing plasma half-life and providing a favorable distribution; (iii) promoting cellular uptake; (iv) facilitating endosome/lysosome escape of siRNA into the cytosol; (v) high biocompatibility/low toxicity; and (vi) absence of unwanted side effects (Whitehead et al. (2009) Nat. Rev. Drug. Discov., 8:129-38). The suppression of mRNA, however, is commonly low in many siRNA polyplexes. Thus, identifying designs and/or modifications that can increase mRNA suppression while satisfying the many other requirements for systemic administration is critical to the development of siRNA polyplexes.

SUMMARY OF THE INVENTION

In accordance with the instant invention, polyplexes are provided. In a particular embodiment, the polyplex comprises at least one short nucleic acid molecule linked (either directly or via a linker) to a hydrophobic moiety and at least one block copolymer comprising a cationically charged polymeric segment and a hydrophilic polymeric segment. The short nucleic acid molecule may be an inhibitory nucleic acid molecule such as an antisense molecule, siRNA, shRNA, DsiRNA, or miRNA. In a particular embodiment, the hydrophobic moiety is cholesterol. In a particular embodiment, the hydrophilic polymeric segment comprises poly(ethylene oxide) and the cationically charged polymeric segment comprises polylysine. The polyplexes of the instant invention may further comprise at least one other bioactive agent, such as a therapeutic agent. Compositions comprising at least one polyplex and at least one pharmaceutically acceptable carrier are also encompassed by the instant invention.

In accordance with another aspect of the instant invention, methods of delivering a nucleic acid molecule to a cell and/or inhibiting expression of a protein are provided. The method comprises contacting the cell with at least one polyplex of the instant invention. The methods may be performed in vitro or in vivo. In a particular embodiment, the method comprises administering (e.g., intravenously) at least one polyplex of the instant invention to a subject. The instant invention also encompasses methods of treating, inhibiting, and/or preventing a disease or disorder in a subject comprising administering at least one polyplex of the instant invention to the subject.

BRIEF DESCRIPTIONS OF THE DRAWING

FIG. 1 shows the minimum N/P ratio for polymer complexation of model siRNA and chol-model siRNA. Model siRNA (dsDNA analog of siRNA; FIG. 1A) or model siRNA modified with 3' cholesterol on a single DNA strand (chol-model siRNA; FIG. 1B) was incubated with the indicated N/P ratio of polymer in 0.1 M HEPES [pH 7.4] for 30 minutes at room temperature and run on a 1% agarose/ethidium bromide gel alongside model siRNA or chol-model siRNA alone (Lane 0). The first N/P ratio where polyplexes are retained in the well indicates charge neutralization of siRNA and is defined as the minimum N/P ratio required for complexation. Data are representative of two independent experiments.

Figure 2:
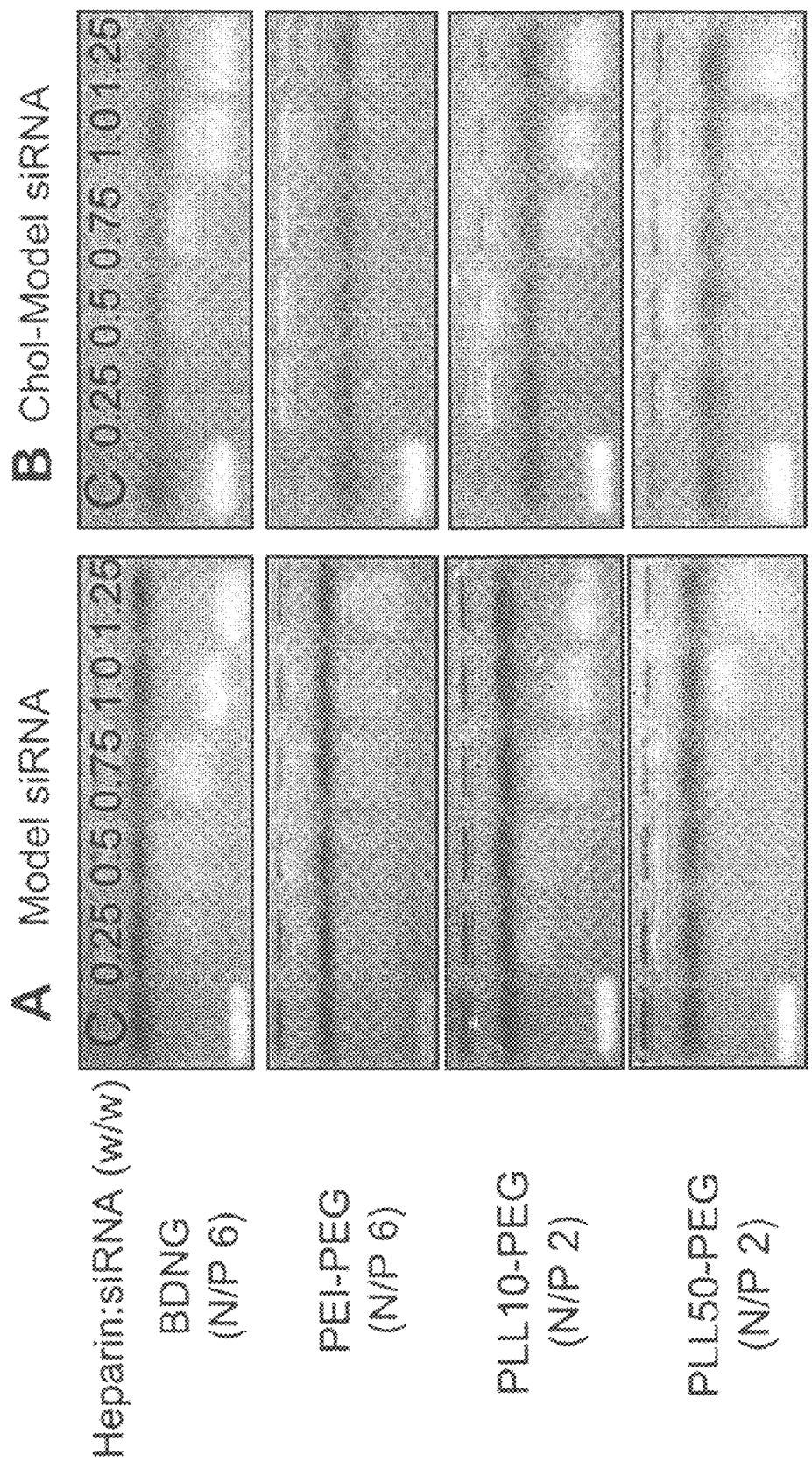

FIG. 2 shows heparin displacement of model siRNA and chol-model siRNA from polyplexes. Model siRNA (dsDNA analog of siRNA; FIG. 2A) or model siRNA modified with 3' cholesterol on a single DNA strand (FIG. 2B) was incubated with polymer in 0.1 M HEPES, pH 7.4 for 30 minutes at room temperature at the indicated minimum N/P ratio required for complexation. Complexes were then incubated with the indicated weight ratio of heparin to siRNA for 30 minutes at room temperature and run on a 1% agarose gel/ethidium bromide gel with model siRNA or chol-model siRNA alone (lane C). Data are representative of two independent experiments.

Figure 3:
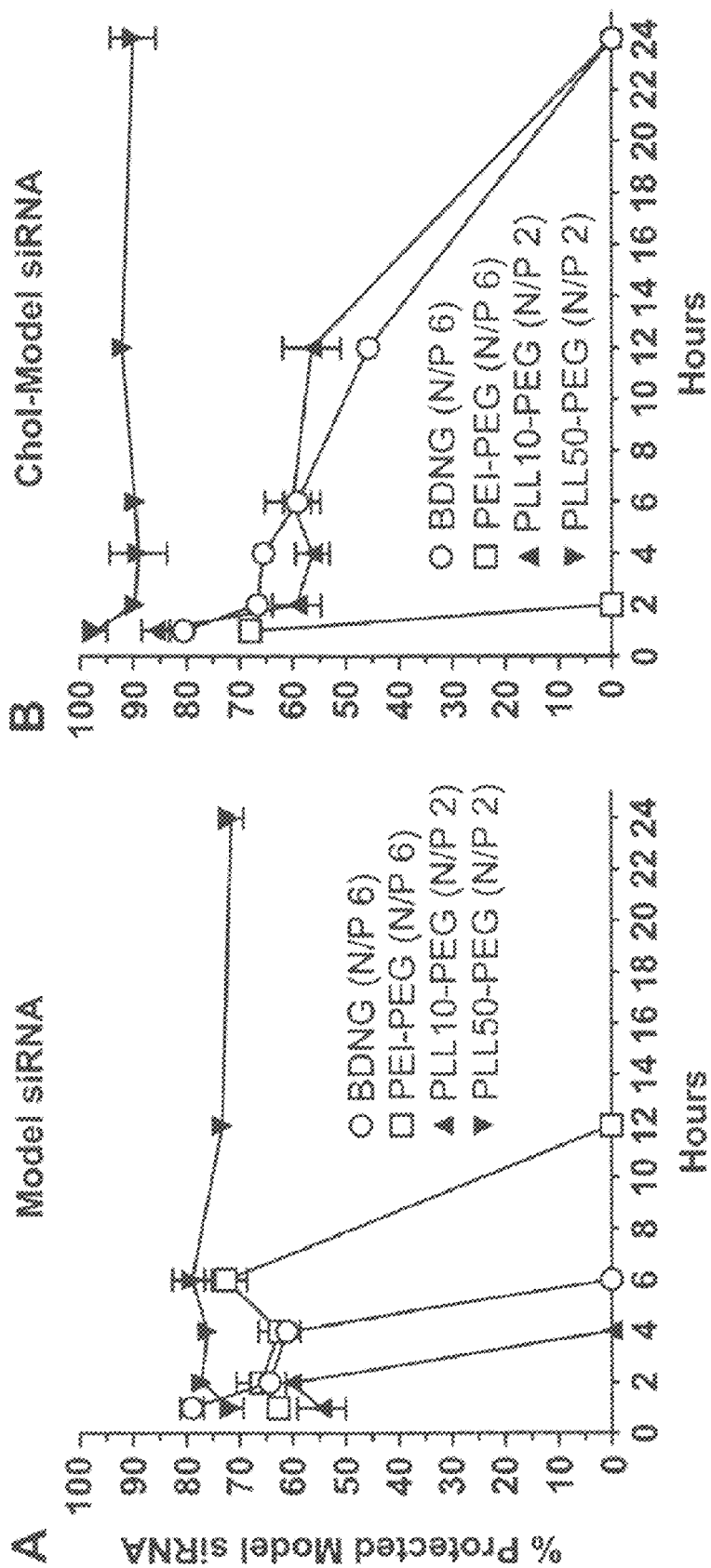

FIG. 3 shows polyplex protection of model siRNA and chol-model siRNA from nuclease activity. Model siRNA (dsDNA analog of siRNA; FIG. 3A) or model siRNA modified with 3' cholesterol on a single DNA strand (FIG. 3B) was incubated with polymer for 30 minutes at room temperature at the indicated minimum N/P ratio required for complexation then incubated in the absence or presence of DNase for the indicated time. Model siRNA and chol-model siRNA were completely degraded within 1 hour under the same conditions. DNase was inactivated and remaining model siRNA was released from the polyplexes by heparin and separated on a 1% agarose/ethidium bromide gel. Bands from DNase-treated polyplexes were quantitated by densitometry and normalized to bands from untreated polyplexes at the same N/P ratio. Percent protected model siRNA±SD (n=2) is an average of two independent experiments.

Figure 4:
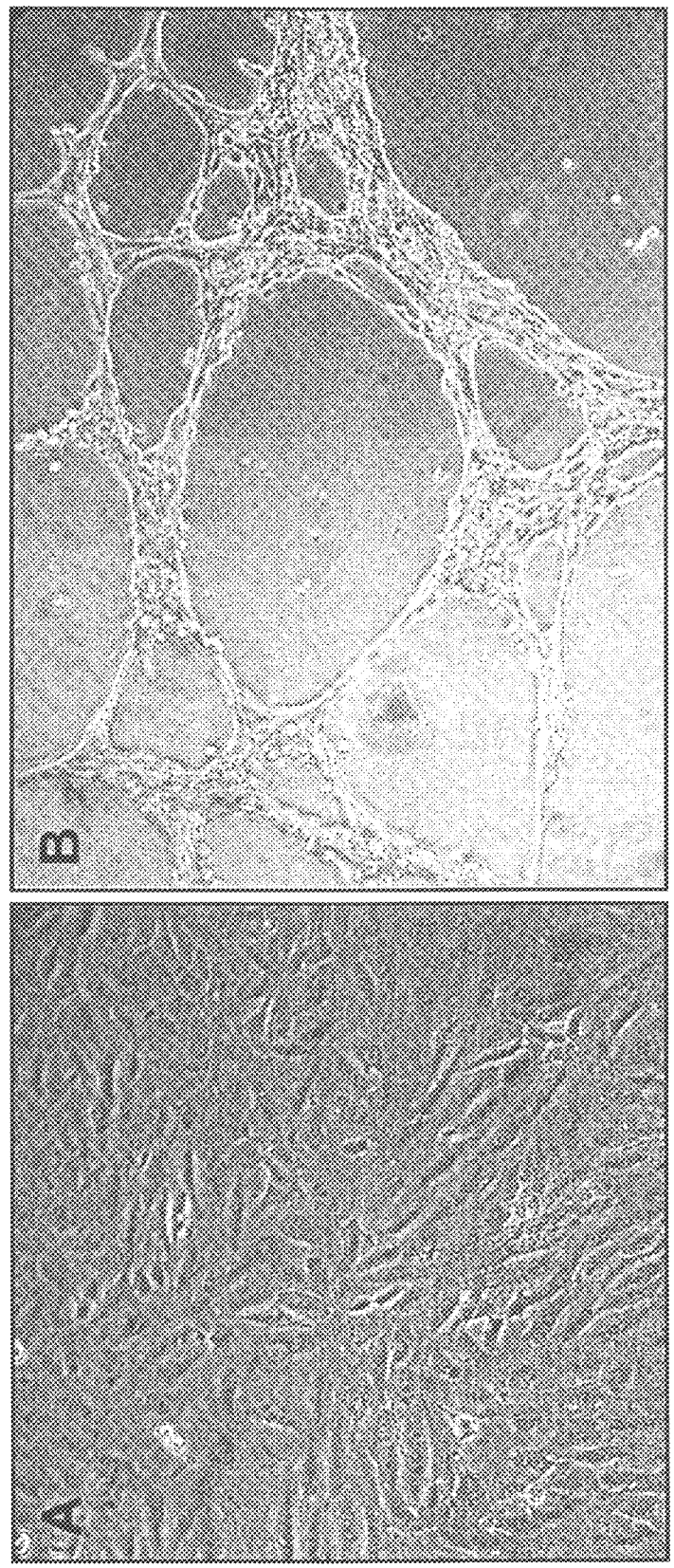

FIG. 4 provides images of homozygous Immortomouse® mammary MVEC. Phase contrast images are provided of mammary MVEC grown at 33° C. in 2D culture (0.2% gelatin; FIG. 4A) and in 3D (Matrigel™) culture (FIG. 4B).

Figure 5:
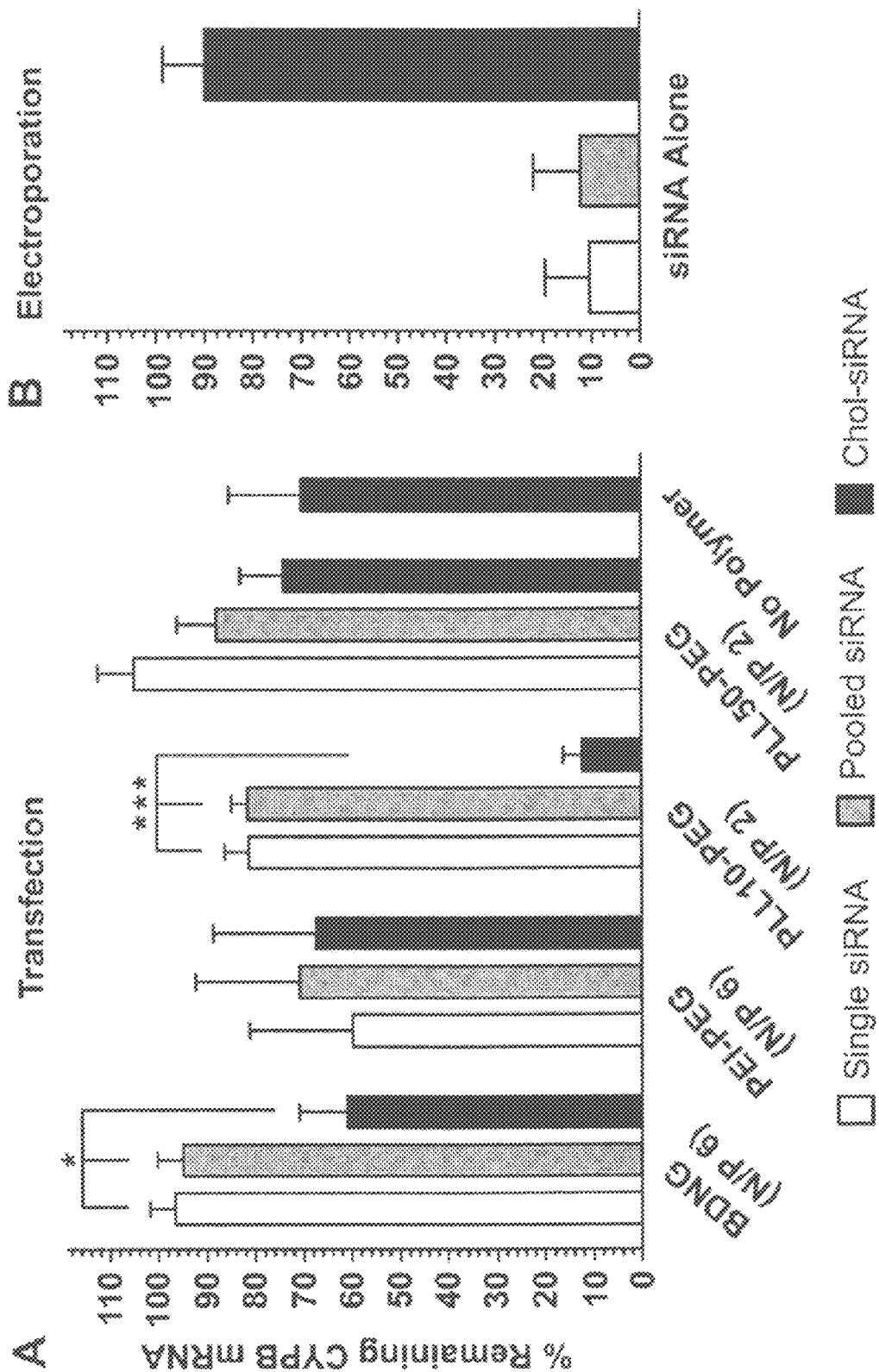

FIG. 5 shows the suppression of native CYPB mRNA in homozygous Immortomouse® mammary MVEC by CYPB siRNA and chol-CYPB siRNA polyplexes 48 hours after transfection. FIG. 5A: conditionally immortalized mammary MVEC (grown at 33° C.) were transfected in 10% complete DMEM for 4 hours with polymer-siRNA complexes (BDNG: N/P 6, PEI-PEG: N/P 6; PLL-PEG: N/P 2) containing single, pooled (4 CYPB siRNA constructs), or chol-CYPB siRNA (3' sense strand) at 100 nM siRNA ($2.5 \times 10^{-15}$ mol siRNA/cell) then media was replaced with 10% complete DMEM. CYPB mRNA levels±SD (n=2) in treated cells were compared to CYPB mRNA from cells treated with the same polyplexes containing single non-targeting siRNA after 48 hours by Q-RT-PCR ($2^{-\Delta\Delta C_t}$ method normalized to GAPDH). "No polymer" is chol-CYPB siRNA alone vs. CYPB siRNA alone. Differences between CYPB siRNA polyplexes and chol-CYPB siRNA polyplexes were determined by one way ANOVA and the Tukeye-Kramer multiple comparison test ($*P<0.05$; $***P<0.001$). FIG. 5B: mammary MVEC were electroporated with 300 nM of siRNA ($6 \times 10^{-17}$ mol siRNA/cell) and CYPB mRNA levels±SD (n=2) in CYPB siRNA treated cells were compared to CYPB mRNA from cells treated with single non-targeting siRNA after 48 hours by Q-RT-PCR ($2^{-\Delta\Delta C_t}$ method normalized to GAPDH). Results are representative of two independent experiments.

Figure 6:
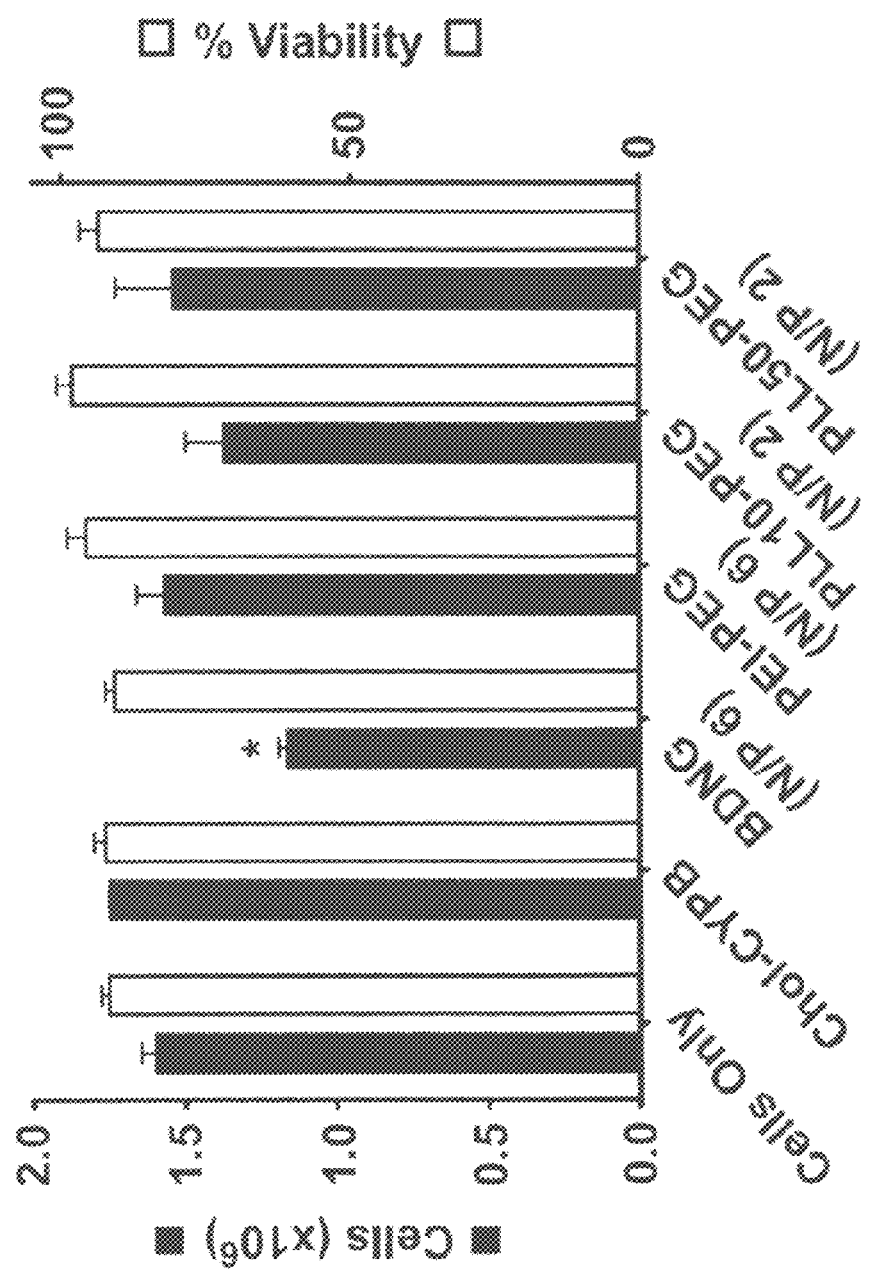

FIG. 6 shows the cytostatic and cytotoxic effects of chol-siRNA polyplexes in homozygous Immortomouse® mammary MVEC 48 hours after transfection. Conditionally immortalized mammary MVEC (grown at 33° C.) were transfected in 10% complete DMEM for 4 hours with or without chol-CYPB siRNA alone (Chol-CYPB) or polymer-siRNA complexes at 100 nM chol-CYPB siRNA ($2.5 \times 10^{-15}$ mol siRNA/cell) then media was replaced with 10% complete DMEM. Average (n=2±SD) total (black bars) and percent viable (white bars) cells were determined by cell counting with trypan blue exclusion after 48 hours. One way ANOVA and Dunnett's post test vs. cells only ($*P<0.05$).

Figure 7A:
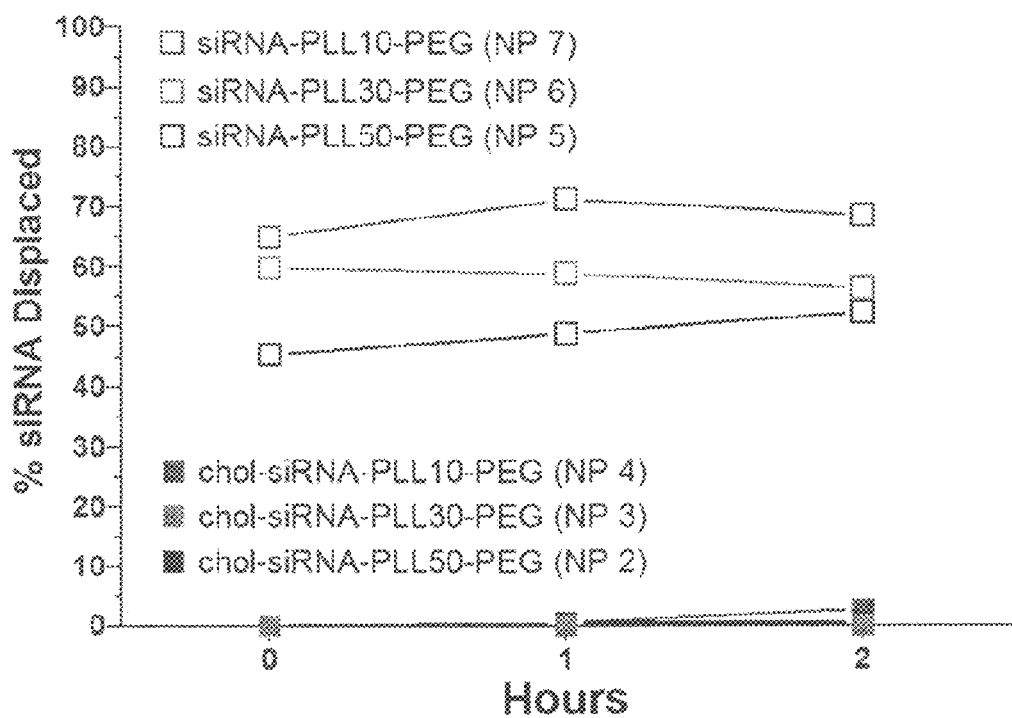
Figure 7B:
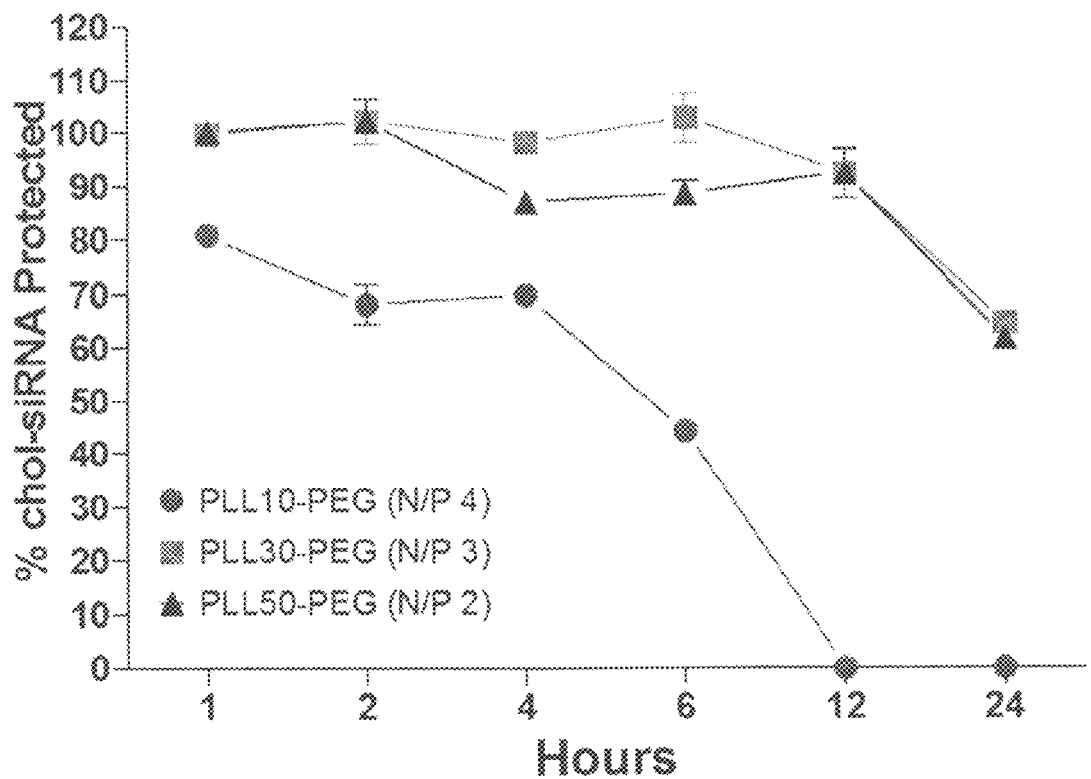

FIG. 7A provides a graph showing the serum displacement of complexed siRNA, optionally modified with 3' cholesterol, from PLL-PEG siRNA polyplexes as a function of PLL block length. FIG. 7B shows the protection of complexed chol-siRNA from serum nuclease activity in 90% serum by polyplexes of PLL-PEG as a function of PLL block length.

Figure 8:
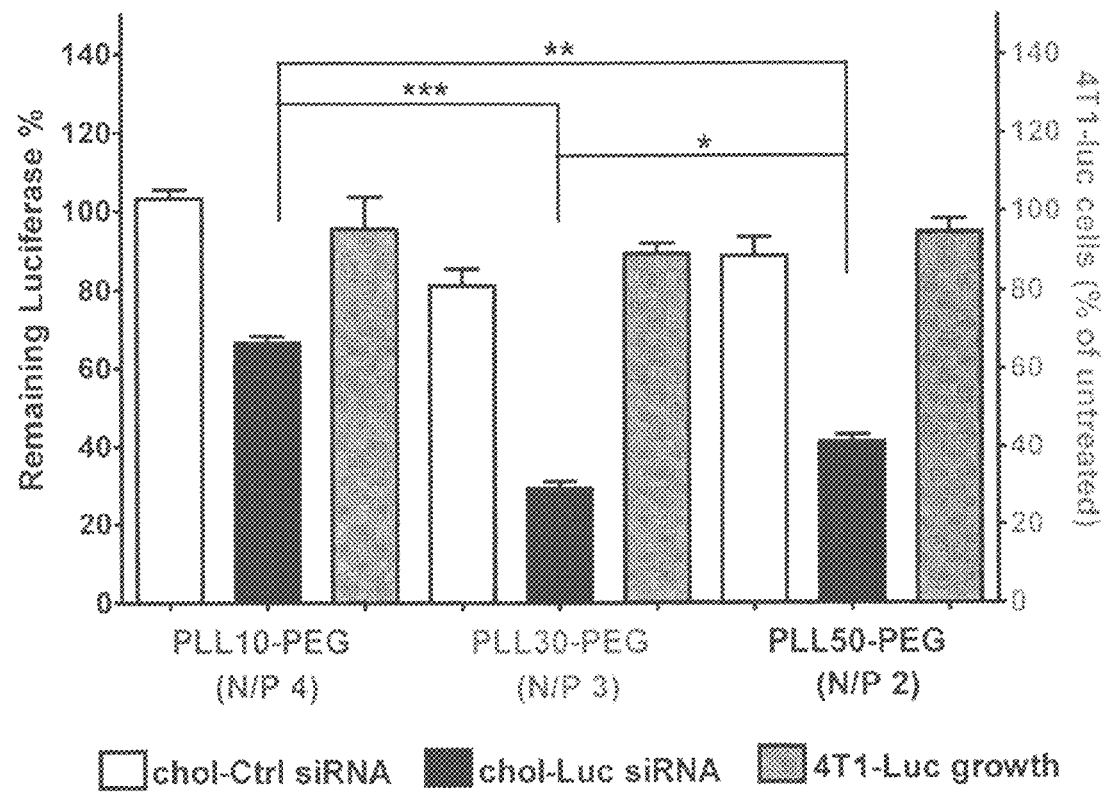
Figure 9A:
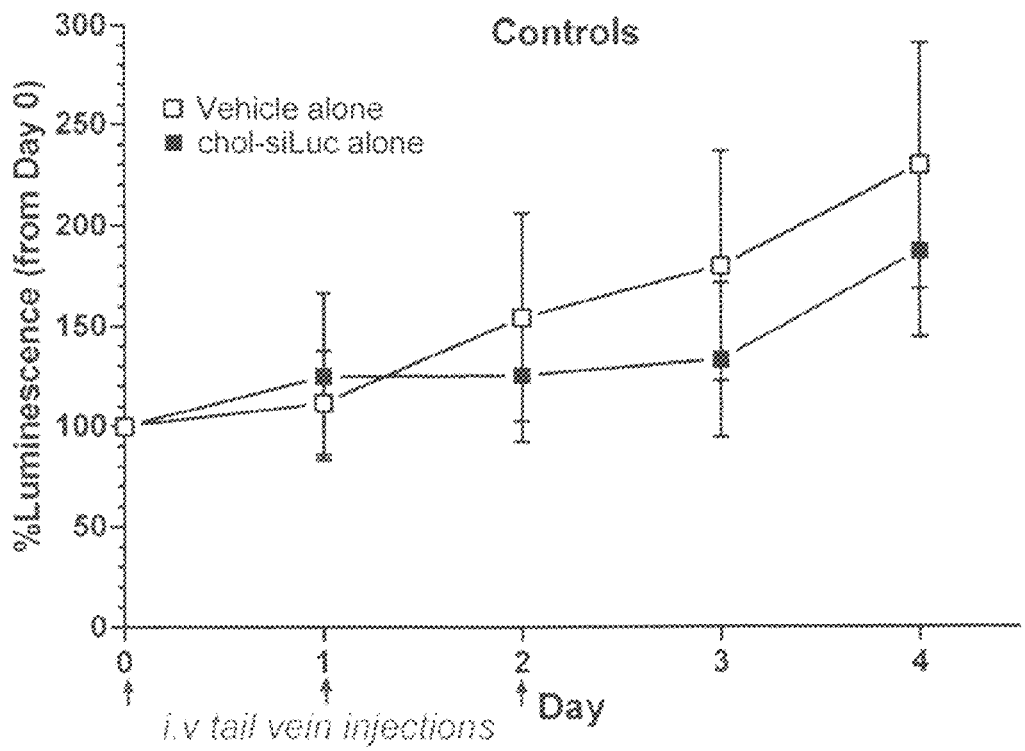
Figure 9B:
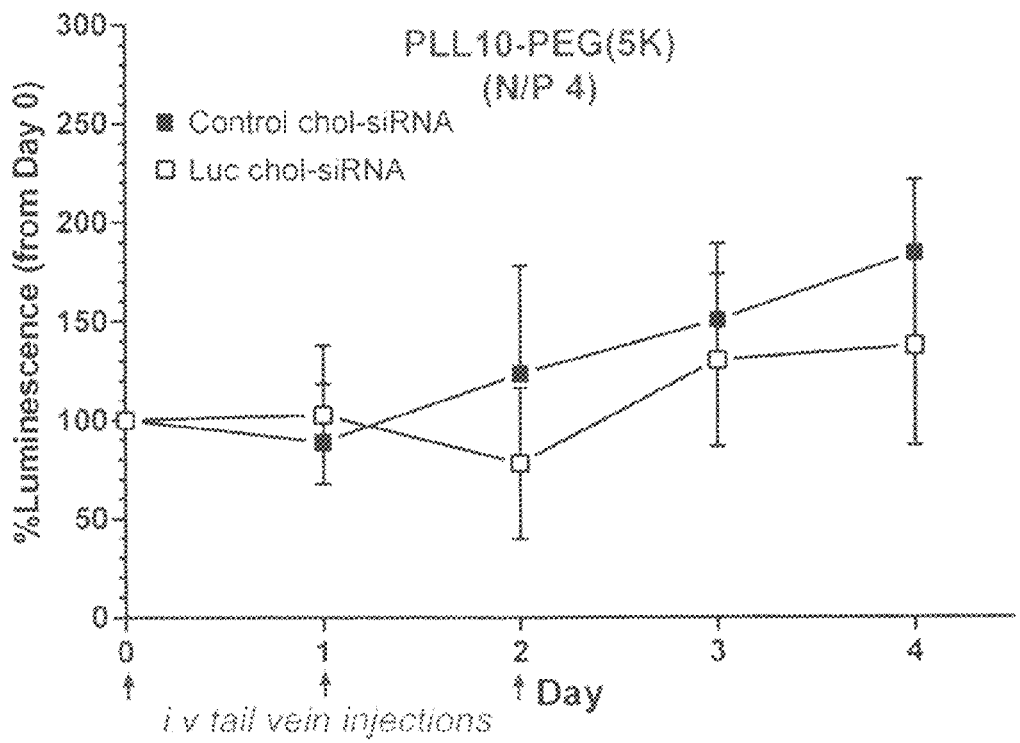
Figure 9C:
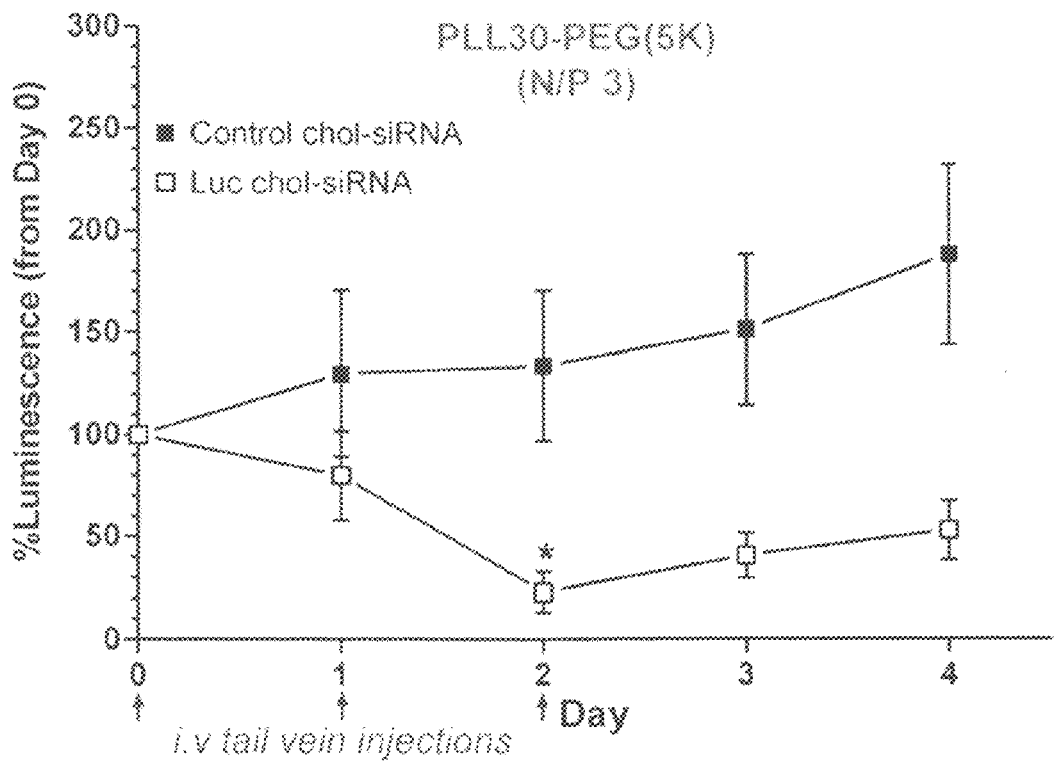
Figure 9D:
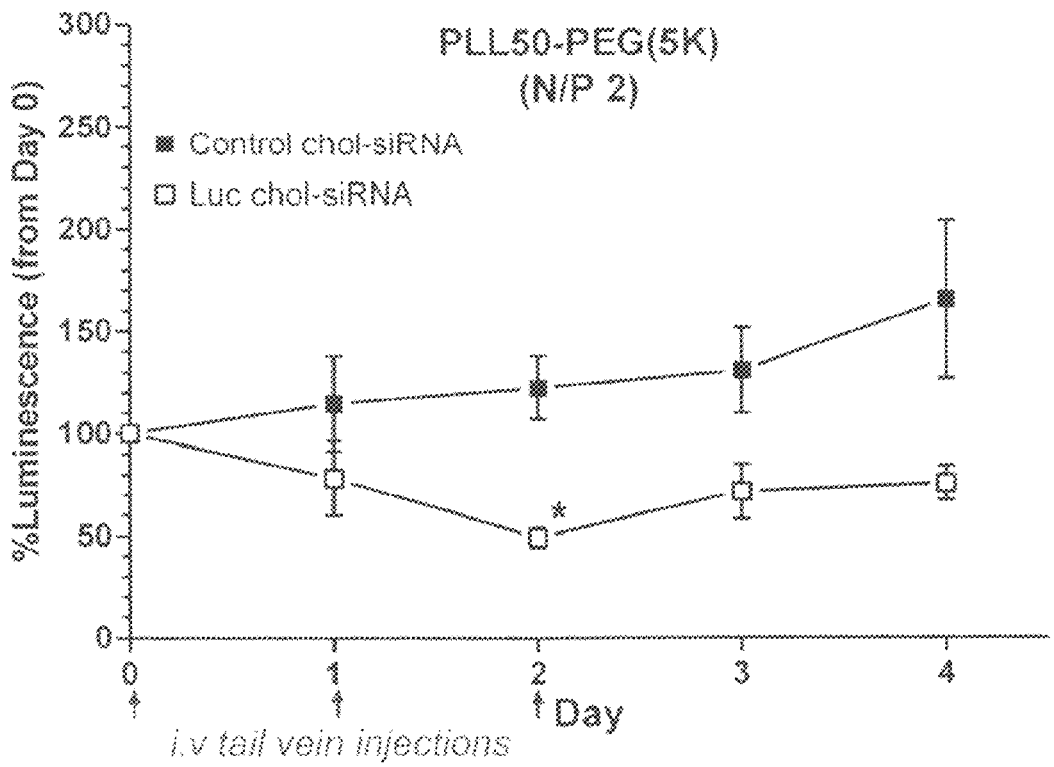
Figure 10A:
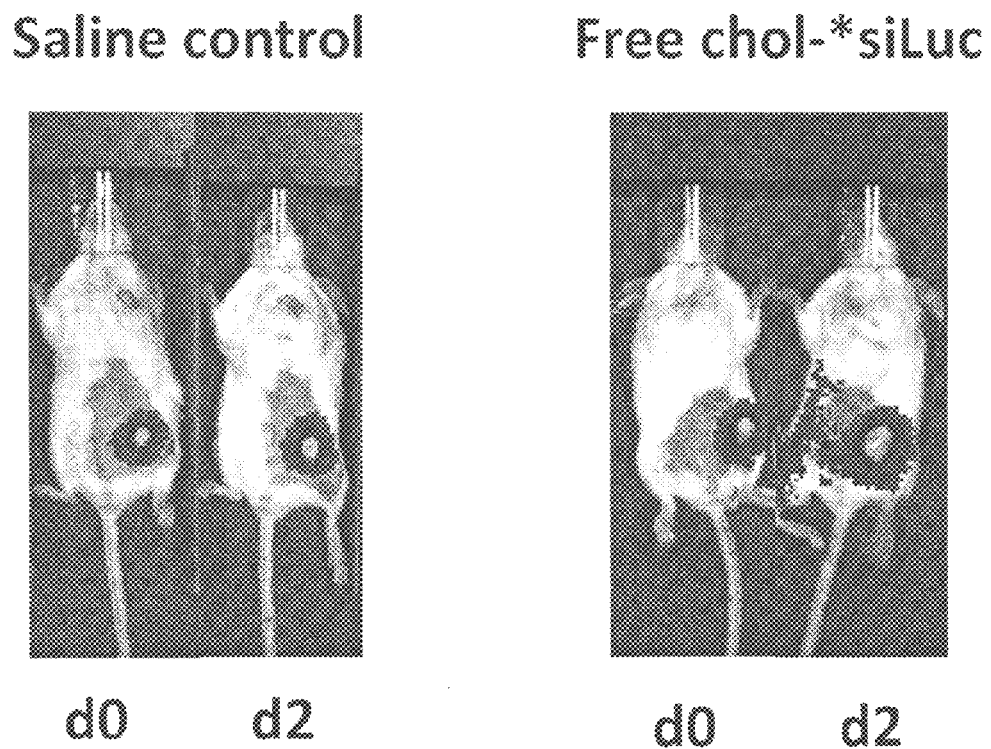
Figure 10B:
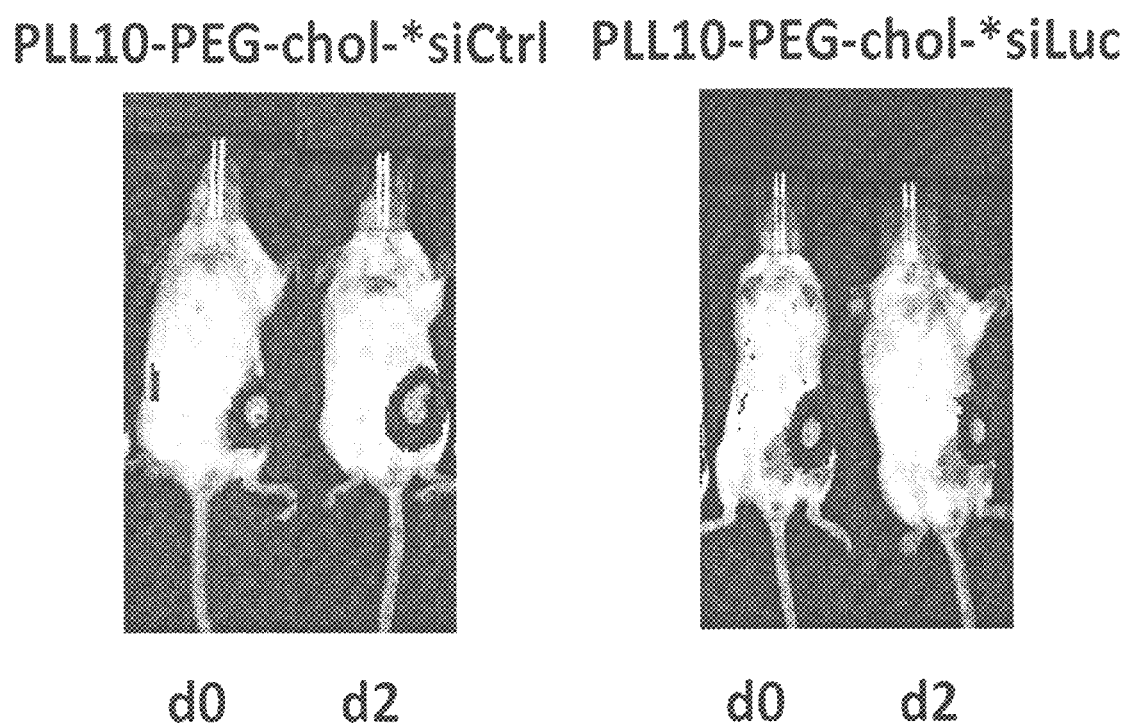
Figure 10C:
Figure 10C:
Figure 10D:
Figure 10D:

FIG. 8 provides a graph showing the suppression of luciferase expression in 4T1-Luc murine breast cancer cells by chol-siRNA polyplexes of PLL-PEG. One way ANOVA and Tukey's post-test were performed ($*p<0.05$, $p<0.01$, $*p<0.001$).

FIGS. 9A-9D provide data showing the in vivo suppression of luciferase mRNA in 4T1-Luc tumors by polyplexes of nuclease-resistant cholesterol-siRNA and PLL30-PEG, PLL30-PEG, or PLL50-PEG. $*p<0.05$ versus average normalized radiance on day 0 within the same treatment group by nonparametric one way ANOVA with Dunn's post-test.

FIGS. 10A-10D present bioluminescent images of mice comprising 4T1-Luc tumors (day 0) or two days after intravenous treatment with the indicated siRNA or polyplexes.

DETAILED DESCRIPTION OF THE INVENTION

Polymer-siRNA complexes (siRNA polyplexes) are being actively developed to improve the therapeutic application of siRNA. A major limitation for many siRNA polyplexes, however, is insufficient mRNA suppression. Modifying the sense strand of siRNA with 3' cholesterol (cholsiRNA) increases the activity of free nuclease-resistant siRNA in hepatoma cells (Huh-7 and Hep G2) in vitro (Lorenz et al. (2004) Bioorg. Med. Chem. Lett., 14:4975-7; Soutschek et al. (2004) Nature 432:173-8) and the liver and jejunum in vivo (Soutschek et al. (2004) Nature 432:173-8). Herein, it is demonstrated that complexation of chol-siRNA increases mRNA suppression by siRNA polyplexes and, as such, is a simple approach to improve siRNA polyplexes for delivery to a subject, e.g., by systemic administration. The characteristics and siRNA activity of self assembled polyplexes formed with chol-siRNA or unmodified siRNA were also compared using three types of conventional, positively charged polymers: (i) biodegradable, cross-linked nanogels (BDNG); (ii) graft copolymers (PEI-PEG); and (iii) linear block copolymers (PLL10-PEG, and PLL50-PEG). Chol-siRNA did not alter complex formation or the resistance of polyplexes to siRNA displacement by heparin but increased nuclease protection by BDNG, PLL10-PEG, and PLL50-PEG polyplexes over polyplexes with unmodified siRNA. Chol-CYPB siRNA increased suppression of native CYPB mRNA in mammary microvascular endothelial cells (MVEC) by BDNG polyplexes and PLL-PEG polyplexes. Overall, these results indicate that complexation of chol-siRNA increases nuclease protection and mRNA suppression by siRNA polyplexes. These results also indicate that polycationic block length is an important factor in increasing mRNA suppression by PLL-PEG chol-siRNA polyplexes in mammary MVEC.

I. Polyplexes

The polyplexes of the instant invention comprise at least one block copolymer and at least one nucleic acid molecule. The block copolymer comprises at least one cationically charged polymeric segment and at least one hydrophilic polymeric segment. In a particular embodiment, the block copolymer has the structure A-B or B-A. Typically, the block copolymer also comprises just the two blocks, but it may comprise more than 2 blocks. For example, the block copolymer may have the structure A-B-A, wherein B is a cationically charged polymeric segment. In a particular embodiment, the segments of the block copolymer comprise about 5 to about 500 repeating units, about 10 to about 300 repeating units, about 10 to about 250 repeating units, about 10 to about 200 repeating units, about 10 to about 150 repeating units, or about 10 to about 100 repeating units.

The cationically charged polymeric segment may comprise polymers and copolymers and their salts comprising units deriving from one or several monomers including, without limitation: primary, secondary and tertiary amines, each of which can be partially or completely quaternized forming quaternary ammonium salts. Examples of these monomers include, without limitation, cationic amino acids (e.g., lysine, arginine, histidine), alkyleneimines (e.g., ethyleneimine, propyleneimine, butyleneimine, pentyleneimine, hexyleneimine, and the like), spermine, vinyl monomers (e.g., vinylcaprolactam, vinylpyridine, and the like), acrylates and methacrylates (e.g., N,N-dimethylaminoethyl acrylate, N,N-dimethylaminoethyl methacrylate, N,N-diethylaminoethyl acrylate, N,N-diethylaminoethyl methacrylate, t-butylaminoethyl methacrylate, acryloxyethyltrimethyl ammonium halide, acryloxyethyl-dimethylbenzyl ammonium halide, methacrylamidopropyltrimethyl ammonium halide and the like), allyl monomers (e.g., dimethyl diallyl ammoniam chloride), and aliphatic, heterocyclic or aromatic ionenes. In a particular embodiment, the cationic polymeric segment comprises cationic amino acids, particularly poly-lysine. In a particular embodiment, the cationic polymeric segment of the block copolymer comprises about 5 to about 100 repeating units, about 10 to about 75 repeating units, about 10 to about 50 repeating units, about 20 to about 50 repeating units, about 20 to about 40 repeating units, or about 30 repeating units.

Examples of hydrophilic polymeric segments include, without limitation, polyetherglycols, poly(ethylene oxide), methoxy-poly(ethylene glycol), copolymers of ethylene oxide and propylene oxide, polysaccharides, polyvinyl alcohol, polyvinyl pyrrolidone, polyvinyltriazole, N-oxide of polyvinylpyridine, N-(2-hydroxypropyl)methacrylamide (HPMA), polyortho esters, polyglycerols, polyacrylamide, polyoxazolines, polyacroylmorpholine, and copolymers or derivatives thereof In a particular embodiment, the hydrophilic polymeric segment comprises poly(ethylene oxide).

The nucleic acid molecules of the polyplexes of the instant invention may be a short nucleic acid molecule such as a short inhibitory nucleic acid molecule (e.g., nucleic acid molecules which specifically hybridize (e.g., are complementary) with a target nucleic acid thereby inhibiting its expression; inhibitory nucleic acid molecules include antisense, siRNA, shRNA, DsiRNA (Dicer siRNA/Dicer-substrate RNA), miRNA (microRNA), etc.). The nucleic acid molecule may be single stranded or double stranded. The nucleic acid molecule may be DNA, RNA, or a mixture. In a particular embodiment, the nucleic acid molecule comprises less than about 100 nucleotides, particularly less than about 50 nucleotides or less than about 30 nucleotides. The nucleic acid molecule may be a probe. The nucleic acid molecules may be conjugated (directly or via a linker) to one or more detectable labels (e.g., for diagnostic or detection methods). The nucleic acid molecules may also comprise at least one nucleotide analog. For example, the nucleotide analog may increase stability and/or resistance to nucleases. For example, the nucleic acid molecules may comprise, without limitation, Locked Nucleic Acid (LNA) bases, nucleotides with phosphate modifications (e.g., phosphorothioates, morpholinos, etc.), nucleotides with modified sugars (e.g., 2'-O-methyl-nucleotides), and nucleotide mimetics (e.g., peptide nucleic acids (PNA), etc.).

The nucleic acid molecules of the instant polyplexes are also conjugated to at least one hydrophobic moiety. The hydrophobic moiety may be conjugated to the nucleic acid molecule at the 5' and/or 3' end of either or both strands of the nucleic acid molecule. In a particular embodiment, the hydrophobic moiety is conjugated only to the 3' end, more particularly the 3' end of the sense strand in double stranded molecules. The hydrophobic moiety may be conjugated directly to the nucleic acid molecule or via a linker. The hydrophobic moiety may be selected from the group consisting of adamantane, cholesterol, steroid, long chain fatty acid, lipid, phospholipid, glycolipid, and derivatives thereof The hydrophobic moiety may be a small molecule. In a particular embodiment, the nucleic acid molecules of the polyplex are conjugated to a cholesterol on the 3' end of the sense strand of the nucleic acid molecule.

Generally, a linker is a chemical moiety comprising a covalent bond or a chain of atoms that covalently attaches two compounds (e.g., the hydrophobic moiety to the nucleic acid molecule). The linker can be linked to any synthetically feasible position of the compounds. Exemplary linkers may comprise at least one optionally substituted; saturated or unsaturated; linear, branched or cyclic alkyl group or an optionally substituted aryl group. In a particular embodiment, the linker may contain from 0 (i.e., a bond) to about 500 atoms, about 1 to about 100 atoms, or about 1 to about 50 atoms. The linker may also be a polypeptide (e.g., from about 1 to about 5). The linker may be non-degradable and may be a covalent bond or any other chemical structure which cannot be substantially cleaved or cleaved at all under physiological environments or conditions.

The polyplexes of the instant invention may also be conjugated to a targeting ligand. A targeting ligand is a compound that will specifically bind to a specific type of tissue or cell type. In a particular embodiment, the targeting ligand is a ligand for a cell surface marker/receptor. The targeting ligand may be any molecule that selectively binds to a cell surface marker (e.g., protein of carbohydrate) preferentially or exclusively expressed on the targeted tissue or cell type (e.g., low molecular weight antagonist (e.g., less than 100 Da, particularly less than about 500 Da), an antibody or fragment thereof, aptamers, peptides, small molecules, etc. The targeting ligand may be linked directly to the polyplex or via a linker. In a particular embodiment, the targeting ligand is linked to the hydrophilic segment of the block copolymer (e.g., at the end).

The polyplexes of the instant invention may be synthesized by contacting at least one block copolymer with at least nucleic acid molecule. The opposite charges of the cationically charged segment of the block copolymer and the anionically charged nucleic acid molecule along with the presence of the hydrophilic segment of the block copolymer allow for self-assembly of the polyplexes in aqueous solutions. In a particular embodiment, the nucleic acid molecule and block copolymer are formed at molar N/P ratios that produce neutralized/electropositive polyplexes. In a particular embodiment, the N/P ratio is from about 1 to about 5. After complex formation, the polyplexes may be purified from non-complexed components by methods known in the art (e.g., size exclusion chromatography, centrifugal filtration, etc.). The resultant polyplexes typically have a diameter less than about 200 nm, particularly less than about 100 nm.

The instant invention also encompasses compositions comprising at least one polyplex of the instant invention and at least one pharmaceutically acceptable carrier. The compositions of the instant invention may further comprise other agents (e.g., bioactive agents) such as therapeutic agents (e.g., chemotherapeutic agents (e.g., paclitaxel)). The polyplexes of the instant invention may comprise at least one other agent (e.g., the polyplexes may encapsulate the agents (e.g., hydrophobic agents) and/or may be conjugated to the agent (e.g., directly or via a linker (e.g., cleavable); e.g., to the block copolymer (e.g., to the cationically charged polymeric segment and/or the hydrophilic segment of the block copolymer, optionally at the ends of the polymer)). The other agent, such as a therapeutic agent or detectable agent (e.g., fluorescent agent), may be a small molecule.

The instant invention also encompasses methods of delivering a nucleic acid molecule to a cell. The method comprises contacting a cell (in vitro or in vivo) with a polyplex of the instant invention. In a particular embodiment, the method comprises administering the polyplex to a subject (e.g., intravenously). The instant invention also encompasses methods of inhibiting expression of a protein in a cell. The method comprises contacting the cell (in vitro or in vivo) with a polyplex of the instant invention, wherein the nucleic acid molecule of the polyplex is an inhibitory nucleic acid molecule. In a particular embodiment, the method comprises administering the polyplex to a subject (e.g., intravenously). The instant invention also encompasses methods of detecting a nucleic acid molecule in a cell. The method comprises contacting a cell (in vitro or in vivo) with a polyplex of the instant invention, wherein the nucleic acid molecule of the polyplex is a probe. In a particular embodiment, the method comprises administering the polyplex to a subject (e.g., intravenously).

The present invention also encompasses methods for preventing, inhibiting, and/or treating a medical condition (e.g., a disease or disorder) in a subject. The pharmaceutical compositions of the instant invention can be administered to an animal, in particular a mammal, more particularly a human, in order to diagnose/treat/inhibit/prevent the medical condition. In a particular embodiment, the medical condition is cancer (e.g., breast cancer, liver cancer, etc.), including metastases. For example, the polyplex may comprise an inhibitory nucleic acid molecule (e.g., an siRNA) which reduces the expression of a protein which is aberrantly expressed in the medical condition (e.g., an oncogene (e.g., HER2/neu in breast cancer). In a particular embodiment, the polyplex comprises at least one probe to detect a nucleic acid molecule associated with the medical condition. The polyplexes, compositions, and methods of the instant invention may also comprise at least one other bioactive agent, particularly at least one other therapeutic agent. Therapeutic agents include, without limitation, polypeptides, peptides, glycoproteins, nucleic acids, synthetic and natural drugs, peptoids, polyenes, macrocyles, glycosides, terpenes, terpenoids, aliphatic and aromatic compounds, small molecules, and their derivatives and salts. While the therapeutic agents are exemplified herein, any bioactive agent may be administered to a patient, e.g., a detectable, diagnostic, or imaging agent. The additional agent may also be administered in separate composition from the polyplexes of the instant invention. The compositions may be administered at the same time or at different times (e.g., sequentially).

II. Administration

The polyplexes described herein will generally be administered to a patient as a pharmaceutical preparation. The term "patient" as used herein refers to human or animal subjects. These polyplexes may be employed therapeutically, under the guidance of a physician or other healthcare professional.

The pharmaceutical preparation comprising the polyplexes of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof The concentration of polyplexes in the chosen medium will depend on the hydrophobic or hydrophilic nature of the medium, as well as the size, enzyme activity, and other properties of the polyplexes. Solubility limits may be easily determined by one skilled in the art.

As used herein, "pharmaceutically acceptable medium" or "carrier" includes any and all solvents, dispersion media and the like which may be appropriate for the desired route of administration of the pharmaceutical preparation, as exemplified in the preceding discussion. The use of such media for pharmaceutically active substances is known in the art. Except insofar as any conventional media or agent is incompatible with the polyplex to be administered, its use in the pharmaceutical preparation is contemplated.

The dose and dosage regimen of a polyplex according to the invention that is suitable for administration to a particular patient may be determined by a physician considering the patient's age, sex, weight, general medical condition, and the specific condition for which the polyplex is being administered and the severity thereof The physician may also take into account the route of administration of the polyplex, the pharmaceutical carrier with which the polyplex is to be combined, and the polyplex's biological activity.

Selection of a suitable pharmaceutical preparation will also depend upon the mode of administration chosen. For example, the polyplex of the invention may be administered by direct injection into a desired area or intravenously. In these instances, the pharmaceutical preparation comprises the polyplexes dispersed in a medium that is compatible with the site of injection.

Polyplexes may be administered by any method such as intravenous injection or intracarotid infusion into the blood stream, oral administration, or by subcutaneous, intramuscular or intraperitoneal injection. Pharmaceutical preparations for injection are known in the art. If injection is selected as a method for administering the polyplexes, steps should be taken to ensure that sufficient amounts of the molecules reach their target cells to exert a biological effect.

Pharmaceutical compositions containing a polyplex of the present invention as the active ingredient in intimate admixture with a pharmaceutical carrier can be prepared according to conventional pharmaceutical compounding techniques. The carrier may take a wide variety of forms depending on the form of preparation desired for administration. Injectable suspensions may be prepared, in which case appropriate liquid carriers, suspending agents and the like may be employed. Additionally, the polyplexes of the instant invention may be administered in a slow-release matrix.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of polyplexes may be determined by evaluating the toxicity of the molecules in animal models. Various concentrations of polyplex pharmaceutical preparations may be administered to mice, and the minimal and maximal dosages may be determined based on the beneficial results and side effects observed as a result of the treatment. Appropriate dosage unit may also be determined by assessing the efficacy of the polyplexes treatment in combination with other standard drugs. The dosage units of polyplexes may be determined individually or in combination with each treatment according to the effect detected.

The pharmaceutical preparation comprising the polyplexes may be administered at appropriate intervals, for example, at least twice a day or more until the pathological symptoms are reduced or alleviated, after which the dosage may be reduced to a maintenance level. The appropriate interval in a particular case would normally depend on the condition of the patient.

III. Definitions

The following definitions are provided to facilitate an understanding of the present invention:

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition resulting in a decrease in the probability that the subject will develop the condition.

As used herein, the term "subject" refers to an animal, particularly a mammal, particularly a human.

A "therapeutically effective amount" of a compound or a pharmaceutical composition refers to an amount effective to prevent, inhibit, treat, or lessen the symptoms of a particular disorder or disease. The treatment of inflammation or infection herein may refer to curing, relieving, and/or preventing the inflammation or infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, the term "purified" or "to purify" refers to the removal of contaminants or undesired compounds from a sample or composition. For example, purification can result in the removal of about 70 to 90%, up to 100%, of the contaminants or undesired compounds from a sample or composition. In certain embodiments, at least 90%, 93%, 95%, 96%, 97%, 98%, 99%, 99.5%, or more of undesired compounds from a sample or composition are removed from a preparation.

The term "alkyl," as employed herein, includes straight, branched, and cyclic chain hydrocarbons containing 1 to about 20 carbons or 1 to about 10 carbons in the normal chain. The hydrocarbon chain of the alkyl groups may be interrupted with one or more oxygen, nitrogen, or sulfur. Examples of suitable alkyl groups include methyl, ethyl, propyl, isopropyl, butyl, t-butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may, optionally, be substituted, preferably with 1 to 4 substituents. The term "lower alkyl" refers to an alkyl which contains 1 to 3 carbons in the hydrocarbon chain. The term "cyclic alkyl" or "cycloalkyl," as employed herein, includes cyclic hydrocarbon groups containing 1 to 3 rings which may be fused or unfused. Cycloalkyl groups may contain a total of 3 to 20 carbons forming the ring(s), particularly 6 to 10 carbons forming the ring(s). Optionally, one of the rings may be an aromatic ring as described below for aryl. The cycloalkyl groups may also, optionally, contain substituted rings that includes at least one (e.g., from 1 to about 4) sulfur, oxygen, or nitrogen heteroatom ring members. Each cycloalkyl group may be, optionally, substituted, with 1 to about 4 substituents. Alkyl substituents include, without limitation, alkyl, alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)-$ or $NHRC(=O)-$, wherein R is an alkyl), urea ($-NHCONH_2$), alkylurea, aryl, ether, ester, thioester, nitrile, nitro, amide, carbonyl, carboxylate and thiol. In a particular embodiment, the substituent is hydrophobic such as an alkyl or aryl.

"Alkenyl" refers to an unsubstituted or substituted hydrocarbon moiety comprising one or more carbon to carbon double bonds (i.e., the alkenyl group is unsaturated) and containing from 1 to about 20 carbon atoms or from 1 to about 10 carbon atoms, which may be a straight, branched, or cyclic hydrocarbon group. The hydrocarbon chain of the alkenyl groups may be interrupted with one or more oxygen, nitrogen, or sulfur. When substituted, alkenyl groups may be substituted at any available point of attachment. Exemplary substituents are described above for alkyl groups.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms, preferably with 1 to about 4 groups. Exemplary substituents are described above for alkyl groups. The aryl groups may be interrupted with one or more oxygen, nitrogen, or sulfur heteroatom ring members (e.g., a heteroaryl).

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "oligonucleotide," as used herein, refers to nucleic acid sequences, primers, and probes of the present invention, and is defined as a nucleic acid molecule comprised of two or more ribo or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10 to about 100 nucleotides, about 10 to about 50 nucleotides, about 15 to about 30 nucleotides, about 15 to about 25 nucleotides, or about 20 to about 50 nucleotides, although it may contain more or fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The phrase "small, interfering RNA (siRNA)" refers to a short (typically less than 30 nucleotides long, more typically between about 21 to about 25 nucleotides in length) double stranded RNA molecule. In a particular embodiment, the siRNA is about 21 nucleotides in length. Typically, the siRNA modulates the expression of a gene to which the siRNA is targeted. The term "short hairpin RNA" or "shRNA" refers to an siRNA precursor that is a single RNA molecule folded into a hairpin structure comprising an siRNA and a single stranded loop portion of at least one, typically 1-10, nucleotide.

As used herein, the term "microRNA" or "miRNA" refers to any type of interfering RNA, including but not limited to, endogenous microRNA (naturally present in the genome) and artificial microRNA. MicroRNA typically have a length in the range of from about 18 to about 30 nucleotides, particularly about 21 to about 25 nucleotides. MicroRNA may be single-stranded RNA molecules. The microRNA may be in the form of pre-miRNA, typically a short stem-loop structure having a length of about 50 to about 90 nucleotides, particularly about 60 to about 80 nucleotides, which are subsequently processed into functional miRNAs.

The term "RNA interference" or "RNAi" refers generally to a sequence-specific or selective process by which a target molecule (e.g., a target gene, protein or RNA) is downregulated via a double-stranded RNA. The double-stranded RNA structures that typically drive RNAi activity are siRNAs, shRNAs, microRNAs, and other double-stranded structures that can be processed to yield a small RNA species that inhibits expression of a target transcript by RNA interference.

The term "Dicer siRNA", "Dicer substrate RNA", or "DsiRNA" refers to oligonucleotides which comprise at least one siRNA molecule and which serve as a substrate for Dicer to release the siRNA molecule, typically 21 nucleotides in length. DsiRNA are double-stranded and comprise RNA or DNA and RNA. Typically, DsiRNA are less than about 100 nucleotides in length, less than about 50 nucleotides in length, less than about 40 nucleotides in length, less than about 35 nucleotides in length, or less than about 30 nucleotides in length. In a particular embodiment, the DsiRNA is 27 nucleotides in length. Examples of DsiRNA are provided in U.S. Patent Application Publication Nos. 2005/0244858; 2005/0277610; 2007/0265220; and 2010/0184841.

The term "antisense" refers to an oligonucleotide having a sequence that hybridizes to a target sequence in an RNA by Watson-Crick base pairing, to form an RNA:oligonucleotide heteroduplex with the target sequence, typically with an mRNA. The antisense oligonucleotide may have exact sequence complementarity to the target sequence or near complementarity. These antisense oligonucleotides may block or inhibit translation of the mRNA, and/or modify the processing of an mRNA to produce a splice variant of the mRNA. Antisense oligonucleotides are typically between about 5 to about 100 nucleotides in length, more typically, between about 7 and about 50 nucleotides in length, and even more typically between about 10 nucleotides and about 30 nucleotides in length.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The terms "detection label" or "detectable agent" refers to a detectable marker that may be detected by a physical or chemical means such as, without limitation, optical, electromagnetic, radiation, fluorescence, photonic, electronic, magnetic, or enzymatic means. Detectable labels include, without limitation, radioisotopes, imaging agents, contrast agents (e.g. paramagnetic or superparamagnetic ions, isotopes (e.g., radioisotopes or stable isotopes), optical agents, and fluorescence agents (e.g., fluorescein and rhodamine and their derivatives).

As used herein, a linker is a chemical moiety comprising a covalent bond or a chain of atoms that covalently attaches two molecules to each other.

As used herein, "diagnose" refers to detecting and identifying a medical condition (e.g., a disease or disorder) in a subject. The term may also encompass assessing or evaluating the medical condition status (progression, regression, stabilization, response to treatment, etc.) in a patient known to have the medical condition.

As used herein, "oncogene" refers to a gene that when it has higher than normal activity (e.g., over-expressed), induces abnormal tissue growth due to effects on the biology of a cell, for example on the cell cycle or cell death process. The term "oncogene" encompasses an overexpressed version of a normal gene in animal cells (the proto-oncogene) that can release the cell from normal restraints on growth (either alone or in concert with other changes), thereby converting a cell into a tumor cell. Examples of human oncogenes include, without limitation: myc, ras, HER-2/neu, Bcl-2, c-Raf kinase, src, EGFR, and the like.

As used herein, the term "small molecule" refers to a substance or compound that has a relatively low molecular weight (e.g., less than 4,000, particularly less than 2,000). Typically, small molecules are organic, but are not proteins, polypeptides, or nucleic acids, though they may be amino acids or dipeptides.

The following examples are provided to illustrate certain embodiments of the invention. They are not intended to limit the invention in any way.

EXAMPLE 1

Materials and Methods
Polymers

BDNG, biodegradable nanogels (named "NG(PEGss)" in (Kohli et al. (2007) J. Control Rel., 121:19-27)) consisting of biodegradable PEI (28 kDa PEI formed from 2 kDa PEI via disulfide bonds) cross-linked with 8 kDa PEG through carbamate bonds, and PEI-PEG, polyethylenimine-g-poly(ethylene) glycol graft copolymer with a cationic block consisting of 2 kDa branched PEI (Sigma, St. Louis, Mo.) and a nonionic hydrophilic block consisting of 10 kDa PEG (Sigma, St. Louis, Mo.) (Vinogradov et al. (1998) Bioconjug. Chem., 9:805-12), were synthesized and purified as described. PLL10-PEG and PLL50-PEG, methoxy-poly(ethylene glycol)-b-poly(L-lysine hydrochloride) block copolymers with cationic blocks consisting of 10 (PLL10) or 50 (PLL50) poly-L-lysine groups and a nonionic hydrophilic block consisting of 5 kDa PEG, were purchased from Alamanda Polymers (Huntsville, Ala.).

siRNA

Model siRNA: Stock solutions of DNA oligonucleotides (IDT, Coralville, Iowa) with two 3' AT overhangs (5'-CTC GAT AGA ATA CAC AGG CAT-3' (SEQ ID NO: 1); 5'-GCC TGT GTA TTC TAT CGA GAT-3' (SEQ ID NO: 2)) in 1× IDT duplex annealing buffer (100 mM potassium acetate, 30 mM HEPES, pH 7.5) were combined to a final concentration of 20 µM, incubated at 95° C. for 5 minutes and cooled at room temperature. Chol-model siRNA: A single RP-HPLC-purified DNA oligonucleotide modified with 3' cholesteryl triethylene glycol (TEG) (5'-CTC GAT AGA ATA CAC AGG CAT/Cholesteryl TEG/-3' (SEQ ID NO: 1)) (IDT, Coralville, Iowa) was annealed to (5'-GCC TGT GTA TTC TAT CGA GAT-3' (SEQ ID NO: 2)) (IDT, Coralville, Iowa) at 20 µM as described for model siRNA. siRNA (with UU overhangs): Lyophilized single CYPB siRNA (Dharmacon D-001820-02: 5'-CAA GUU CCA UCG UGU CAU C-3' (SEQ ID NO: 3)), single chol-CYPB siRNA (Dharmacon D-001820-02 modified with cholesterol through a 6 carbon hydroxyproline linker and purified by RP-HPLC), pooled CYPB siRNA (Dharmacon D-001820-20: 5'-CAA GUU CCA UCG UGU CAU C-3' (SEQ ID NO: 4); 5'-CGG CAA AGU UCU AGA GGG C-3' (SEQ ID NO: 5); 5'-GGA GAA ACC CUU CGC CAU U-3' (SEQ ID NO: 6); 5'-GAA AGA GCA UCU AUG GUG A-3' (SEQ ID NO: 7)) against murine CYPB mRNA (NM_011149), and single non-targeting siRNA (Dharmacon D-001810-01: 5'-UGG UUU ACA UGU CGA CUA A-3' (SEQ ID NO: 8)) were resuspended according to manufacturer's instructions in 1× Dharmacon Buffer at 20 µM and stored in aliquots at −80° C.

Model siRNA Loading

Model siRNA polyplexes were formed by adding 10 µL of model siRNA or chol-model siRNA (20 µg/mL [1.556 mM] in 0.1 M HEPES Buffer [pH 7.4]) to 10 µL of HEPES buffer alone (N/P=0) or 10 mL of HEPES buffer containing polymer at the indicated N/P ratio and incubating at room temperature for 30 minutes. N/P ratio was calculated as a ratio between the positively charged groups of a polymer (amines—N) and negatively charged nucleic acids such as siRNA (phosphates—P). N/P molar ratios were calculated using moles PLL-PEG primary amines (PLL10-PEG: 1.5 mmol 1' amine/mol polymer; PLL50-PEG: 3.79 mmol 1' amine/mol polymer) or moles total nitrogen (PEI-PEG: 2.65 mmol N/g polymer; BDNG: 4.4 mmol N/g polymer) to moles siRNA phosphates (42 mol phosphate/mol model siRNA). Polyplexes were loaded (10 mL) on a 1% TBE agarose gel (UltraPure™ Agarose-1000, Invitrogen/ethidium bromide [0.5 µg/mL]), run at 120 V for 15 minutes, and imaged under UV trans-illumination using a Molecular Imager® ChemiDoc™ XRS (BioRad, Hercules, Calif.).

Model siRNA Displacement Assay

Model siRNA polyplexes were formed as described above at the minimum N/P ratio required for complexation, then incubated with 5 µL of heparin sodium (196 U/mg Sigma, St.

Louis, Mo.; 10-100 μg heparin sodium/mL in 0.1 M HEPES buffer, pH 7.4) for 30 minutes at room temperature and analyzed on an agarose gel alongside model siRNA or chol-model siRNA alone.

Model siRNA Nuclease Protection Assay

Model siRNA polyplexes were formed as described above at minimum N/P ratio required for model siRNA complexation, then incubated with 1 μL 1 U/mL Turbo™ DNase (Ambion, Austin, Tex.) or 1 μL 0.1 M HEPES [pH 7.4] for the indicated times at 37° C. DNase was inactivated by heating the solutions at 90° C. for 15 minutes in the presence of 15 mM EDTA. Model siRNA was released by adding 4 μL of 1000 U heparin/mL (20 IU heparin/μg model siRNA) and run on an agarose gel as described above. Model siRNA (dsDNA) bands from treated polyplexes were quantitated by densitometry (Quantity One® software, BioRad) and normalized to bands from untreated polyplexes at the same N/P ratio. Percent protected model siRNA was expressed as [(average density of band from treated complex)/(average density of band from the untreated complex of the same polymer)]×100.

Polyplex Hydrodynamic Diameter by Dynamic Light Scattering

The hydrodynamic diameters of model siRNA and chol-model polyplexes in 0.1 M HEPES [pH 7.4] at 1 mg polymer/mL and indicated N/P ratio were measured by Dynamic Light Scattering (DLS) using a ZetaSizer Nano ZS (Malvern Instruments, Malvern, UK) equipped with He—Ne laser ($\lambda$=633 nm) as the incident beam. Average polyplex diameters (n=3 measurement±SD) with model siRNA and chol-model siRNA were compared by unpaired t-test (P<0.05).

Isolation of Immortomouse® Mammary Cells

Isolation procedures were performed with slight modification (Langley et al. (2003) Cancer Res., 63:2971-6) and approved by IACUC following appropriate guidelines. Surgical instruments were sterilized O/N in Spectra-Soak™, then rinsed with Mince Buffer (HBSS, Amphotericin B [5.0 μg/mL], Gentamycin [50 μg/mL], Penicillin G [100 U/mL], Streptomycin Sulfate [100 μg/mL]) at least 10 minutes before use. Four nulliparous, 6-8 week old homozygous female H-2$K^b$-ts-A58 mice (Immortomouse®, Charles River Labs, Wilmington, Mass.) were euthanized, then hair from the dorsal side was shortened with an electric shaver and Nair® was applied for 4 minutes before removal with a sterile sponge. Nair®-treated areas were sprayed with 70% ethanol and remaining hair removed with a new sterile sponge. Mammary fat pad was resected and pooled into a 100×20 mm culture dish with 10 mL of Mince Buffer, moved to a fresh 100×20 mm culture dish containing 10 mL of Mince Buffer and cut with new sterile scalpels into 1 mm sized fragments. Fragments were incubated in 10 mL of 0.2% Collagenase Type 1 (Worthington Biochemical Co., Lakewood, N.J.) for 60 minutes at 37° C. then centrifuged at 400× g for 10 minutes. The pellet was washed 2× with 20% Complete DMEM (DMEM, FBS 20% [Atlanta Biologicals (Atlanta, Ga.), endotoxin<0.3 EU scale, heat-inactivated by incubation at 56° C. for 30 minutes and cooling in an ice bath], 1 mM L-glutamine, 2 mM Glutamax™, 1 mM sodium pyruvate, 0.1 mM non-essential amino acids, 1× vitamins, 5.0 μg/mL amphotericin B [Fungizone™], 50 μg/mL gentamycin, 100 U/mL penicillin G, 100 μg/mL streptomycin sulfate), resuspended in 2 mL Complete DMEM, and cultured at 33° C., 5% $CO_2$, in a single well of a 6-well plate precoated with 1% gelatin in D-PBS. Unlike previous studies (Jat et al. (1991) Proc. Natl. Acad. Sci., 88:5096-100; Takacs-Jarrett et al. (2001) Am. J. Physiol. Cell Physiol., 280:C228-36; Sweeney et al. (2001) Am. J. Physiol. Cell Physiol., 281:C1695-705; Dory et al. (2003) J. Leukoc. Biol., 74:49-59), IFN-γ was not added to avoid possible long term effects on MVEC surface and function. Colonies were observed 10-20 days later. For routine expansion, cells were cultured in 10% FBS Complete DMEM at 33° C., 5% $CO_2$, in 0.2% gelatin-coated flasks and passaged at no greater than a ¼ split using Accutase™ (Sigma, St. Louis, Mo.).

Isolation of Immortomouse® Mammary MVEC

Mammary MVEC were isolated from heterogeneous populations of homozygous Immortomouse® mammary cells by FACS, double staining for TNF-α-inducible (20 μg murine TNF-α (Peprotech)/mL at 33° C. for 4-6 hours) V-CAM-1/E-Selectin expression (Langley et al. (2003) Cancer Res., 63:2971-6) using FITC-labeled Rat anti-mouse CD106/V-CAM-1 (1.5 μg/1×10$^6$ cells; Clone M/K-2: Southern Biotech, Birmingham, Ala.) and R-PE-conjugated Rat anti-mouse CD62E/E-Selectin (3.0 μg/1×10$^6$ cells; Clone 10E9.6: BD Biosciences, San Jose, Calif.). Sorted cells were plated in a single well of a 6-well plate coated with 0.2% gelatin in D-PBS and passaged upon confluence as described for mammary cells and not used beyond passage 20.

Matrigel™ Assay

Matrigel™ Matrix High concentration (4 mg/mL in DMEM; BD Biosciences) was thawed on ice at 4° C. overnight. The next day, 50 μL of Matrigel™ was added with ice-cooled tips to each well of an ice-cooled 96-well plate and incubated at 37° C. for 1 hour, mammary MVEC were then added to Matrigel™ at 2×10$^4$ cells in 10% complete DMEM (50 mL, 4×10$^5$ cells/mL) and grown at 37° C.

Suppression of CYPB mRNA in Mammary MVEC by siRNA Polyplexes

Homozygous Immortomouse® mammary MVEC were seeded in a 24-well plate at 20,000 cells/well and incubated at 33° C. 24 hours before transfection. On the day of transfection, polymers were sterilized under vacuum for 2 hours in a desiccator containing a glass dish of 95% alcohol, resuspended in 0.1 M HEPES buffer (pH 7.4), sonicated for 10 minutes, and spun at 16,100×g for 10 minutes. A stock solution of siRNA (20 μM) was added to different stock solutions of polymer to form siRNA polyplexes at the appropriate N/P ratio and mixed. The mixture was incubated at RT for 30 minutes, then diluted 1/100 in 10% Complete DMEM to give a final concentration of 100 nM siRNA. Mammary MVEC were incubated with 500 μL of polymer-siRNA complexes (2.5×10$^{-15}$ mol siRNA/cell) for 4 hours and media replaced with Complete DMEM. After 44 hours (48 hours from starting treatment), total RNA was isolated using the FastLane cDNA kit (Qiagen, Valencia, Calif.) according to manufacturer's instructions. RNA from two independent treatments was combined and quantitated by measuring A260 using a BioPhotometer™ (Eppendorf, Hamburg, Germany). All samples were normalized to the lowest concentration of RNA obtained. Complementary DNA (cDNA) was synthesized from 4 μL of the normalized RNA samples using FastLane cDNA kit according to manufacturer's instructions. Relative levels of CYPB mRNA were determined from cDNA by real time PCR (iCycler iQ™ Real Time PCR Detection System, BioRad) using murine GAPDH and CYPB primer assays (Qiagen) and QuantiFast™ SYBR® Green PCR kit (Qiagen) according to manufacturer's instructions. Amplified bands were verified by Tm (melting curves) and size (agarose gel). Levels of CYPB in cells treated with polyplexes containing active siRNA were normalized to the levels of CYPB in cells treated with polyplexes containing single non-targeting siRNA and calculated using the $2^{-\Delta\Delta Ct}$ method (Schmittgen et al. (2008) Nat. Protoc., 3:1101-8) and expressed as percent relative suppression of CYPB mRNA. Differences between CYPB siRNA polyplexes and chol-CYPB siRNA polyplexes (n=2) mRNA suppression were determined by one way ANOVA and the Tukeye-Kramer multiple comparison test.

Relative Suppression of CYPB mRNA in Mammary MVEC by Electroporation

Homozygous Immortomouse® mammary MVEC (70-80% confluent) were electroporated with single CYPB siRNA, pooled CYPB siRNA, chol-CYPB siRNA or single non-targeting siRNA using a Nucleofector™ (Lonza AG, Bazel, Switzerland) on setting T-023 and a Basic Nucleofector™ Kit for Mammalian Endothelial Cells (VPI-1001) with 300 nM siRNA and $5 \times 10^6$ cells/mL ($6 \times 10^{-17}$ mol siRNA/cell) according to manufacturer's instructions. Relative levels of CYPB mRNA were determined after 48 hours as described above.

Cytotoxicity of siRNA Polyplexes in Mammary MVEC

Cells were treated in the same manner as described above using polyplexes of single chol-CYPB siRNA except that total live cell count and percent viability were determined 48 hours after transfection with Trypan Blue using a Cellometer® Auto T4 (Nexcelom Bioscience, Lawrence, Mass.) according to manufacturer's instructions. Differences in cell count and percent cells excluding trypan blue were assessed by one way ANOVA and Dunnett's post test vs. cells only.

Results

Formation of chol-siRNA Polyplexes siRNA polyplex designs are commonly based on the self assembly of positively charged polymers (amines—N) and negatively charged nucleic acids such as siRNA (phosphates—P) formed at different ratios of polymer (N) to nucleic acid (P) (N/P ratios) (Aigner, A. (2008) Curr. Pharm. Des., 14:3603-19). Nucleic acids frequently have higher activity in polyplexes formed at N/P ratios that produce neutralized/electropositive polyplexes. As such, any change in the N/P ratio that forms neutralized/electropositive siRNA polyplexes may affect subsequent mRNA suppression.

To determine whether chol-siRNA significantly alters self assembly, the minimum N/P ratios required to form neutral/electropositive polyplexes of model siRNA and chol-model siRNA were compared (FIG. 1). Polyplexes were formed from three general types of conventional, positively charged polymer constructs: (i) biodegradable, cross-linked nanogels; (ii) graft copolymers; and (iii) linear block copolymers (Table 1). The specific polymers were chosen because they were expected to minimally form stable polyplexes in solution (PLL10-PEG and PLL50-PEG) or form stable polyplexes that may potentially increase mRNA suppression (BDNG and PEI-PEG) through the presence of PEI (Boussif et al. (1995) Proc. Natl. Acad. Sci., 92:7297-301; Sonawane et al. (2003) J. Biol. Chem., 278:44826-31). Given that dsDNA is comparatively inexpensive, less susceptible to background nuclease activity, and has an equivalent charge density and similar structure to siRNA (dsRNA), a model siRNA composed of 19 by dsDNA with two 3' nucleotide overhangs on each strand and a model siRNA modified with 3' cholesterol on one of the DNA strands (chol-model siRNA) were used as analogs of siRNA and chol-siRNA, respectively, for all characterization studies.

TABLE 1

| Polymer constructs. | | |
|---|---|---|
| Polymer | Description | Ref. |
| BDNG | Biodegradable PEI (28 kDa PEI: 2 kDa PEI linked by disulfide bonds) cross-linked with 8 kDa PEG through carbamate bonds | Kohli et al. (2007) J. Control Rel., 121: 19-27 |
| PEI-PEG | Graft copolymer of branched polyethylenimine (2 kDa) and poly(ethylene)glycol (10 kDa) | Vinogradov et al. (1998) Bioconjug. Chem., 9: 805-12 |
| pLL10-PEG | Block copolymer of poly-L-lysine (10 Lys) and PEG (5 kDa) | Alamanda Polymers |
| pLL50-PEG | Block copolymer of poly-L-lysine (50 Lys) and PEG (5 kDa) | Alamanda Polymers |

BDNG and PEI-PEG neutralized model siRNA at N/P ratios≥6 (BDNG: 18.37 wt. % and PEI-PEG: 11.9 wt. % siRNA), whereas both PLL-PEG polymers neutralized model siRNA at N/P ratios≥2 (PLL10-PEG: 18.7 wt. % and PLL50-PEG: 36.7 wt. % siRNA) (FIG. 1A) as polyplex migration was observed at N/P ratios<2. The same patterns were observed with polyplexes of chol-model siRNA (FIG. 1B). Thus, chol-model siRNA does not increase the minimum N/P ratio to form neutral/electropositive siRNA polyplexes. It remains possible that chol-model siRNA decreases the minimum N/P ratio for neutralizing siRNA by less than the 1 M N/P increment used in this assay. As such, chol-siRNA may decrease the N/P ratio to form neutral/electropositive siRNA polyplexes but cannot be determined from these results. The same minimum N/P ratios for siRNA and chol-siRNA, however, formed neutral/electropositive polyplexes and, as such, were suitable for use in subsequent studies.

Resistance of chol-siRNA Polyplexes to Displacement by Heparin

Polyanions disassemble DNA polyplexes in vitro (Moret et al. (2001) J. Control Rel., 76:169-81; Bertschinger et al. (2006) J. Control Rel., 116:96-104). Thus, polyanions attached to cell surface proteoglycans, such as heparan sulfate, have the potential to disassemble siRNA polyplexes, leading to the release of siRNA upon interactions with the interior of blood vessels or other cell surfaces.

To determine whether modification of siRNA with 3' cholesterol increases the resistance of siRNA polyplexes to disassembly by polyanions, the concentration-dependent displacement of model siRNA and chol-model siRNA from polyplexes by a model of heparan sulfate, heparin, was compared at the minimum N/P ratios to form neutral/electropositive siRNA polyplexes (FIG. 2). The pattern of heparin displacement of model siRNA from each polyplex (FIG. 2A) was similar to the pattern of heparin displacement of chol-model siRNA (FIG. 2B). Furthermore, the weight ratio of heparin to siRNA that completely released model siRNA and chol-model siRNA from each polyplex was the same: 1.25:1 for BDNG, PLL10-PEG, and PLL50-PEG (FIGS. 2A and B) and 2:1 for PEI-PEG. Thus, chol-model siRNA does not increase the resistance of these polyplexes to the displacement of siRNA by heparin.

It remains possible that chol-model siRNA decreases the weight ratio of heparin to siRNA for complete siRNA release by less than the heparin increment used in this assay. Thus, chol-siRNA may decrease the resistance of polyplexes to siRNA release by heparin but cannot be determined from these results.

Chol-siRNA Polyplex Protection Against Nuclease Degradation

Systemic nucleases greatly decrease the plasma half-life of siRNA (Hannon et al. (2004) Nature 431:371-8). Thus, it is important to form polyplexes that provide long term protection from nuclease degradation to allow time for the polyplexes to accumulate in the target cells after systemic administration. Given that the hydrophobic 3' cholesterol moieties are likely to interact, it is possible that the arrangement of siRNA within chol-siRNA polyplexes will be different and change polyplex protection against nuclease activity.

To determine whether modifying siRNA with 3' cholesterol changes polymer protection of siRNA from nuclease degradation under maximal loading conditions, polyplexes were formed with model siRNA or chol-model siRNA at the minimum N/P ratio required to form neutral/electropositive polyplexes and resistance to nuclease activity over 24 hours was compared (FIG. 3). Model siRNA and chol-model siRNA were completely degraded within an hour under these conditions and were used to more easily identify differences in nuclease protection by each polyplex.

Chol-model siRNA increased the duration of nuclease protection by PLL10-PEG polyplexes the most (at least 8 hours) as model siRNA was undetectable after 4 hours (FIG. 3A), whereas chol-model siRNA was undetectable after sometime between 12 and 24 hours (FIG. 3B). The duration of nuclease protection by BDNG also increased (at least 6 hours), as model siRNA was undetectable after 6 hours, whereas chol-model siRNA was undetectable after sometime between 12 and 24 hours. The duration of nuclease protection by PLL50-PEG was unchanged over the course of the study due to high levels of protection for both unmodified and chol-model siRNA, but the extent of chol-model siRNA protected after 24 hours increased 19% (71±2% model siRNA vs. 90±4% chol-model siRNA, n=2, P<0.01). In contrast, chol-model siRNA decreased the duration of nuclease protection by PEI-PEG (FIG. 3).

Considering that the amount of protected model siRNA or chol-model siRNA did not change over 24 hours, it is unclear whether increased nuclease protection by chol-siRNA PLL50-PEG polyplexes is due to a slower rate of siRNA degradation or an increase in siRNA that is inaccessible to nuclease activity. Thus, chol-siRNA selectively increases the duration and/or, in the case of PLL50-PEG, the extent of nuclease protection by these polyplexes at the minimum N/P ratio to form neutral/electropositive polyplexes.

Chol-siRNA Effect on Polyplex Hydrodynamic Diameters

Given that the hydrophobic 3' cholesterol moieties of chol-siRNA are likely to interact within chol-siRNA polyplexes, the arrangement of "soft nanomaterials" such as siRNA polyplexes may be altered and reflected as a change in the hydrodynamic diameter. Chol-model siRNA decreased the hydrodynamic diameters of PEI-PEG, PLL10-PEG, and PLL50-PEG polyplexes but increased the hydrodynamic diameter of BDNG siRNA polyplexes (Table 2). Thus, chol-siRNA changes the hydrodynamic diameters of these siRNA polyplexes.

TABLE 2

Hydrodynamic diameters of model siRNA and chol-model siRNA polyplexes.

| Polyplex | Hydrodynamic Diameter (nm ± SD) | |
| --- | --- | --- |
| | Model siRNA | Chol-model siRNA[a] |
| BDNG (N/P 6) | 114 ± 2 | 169 ± 2 |
| PEI-PEG (N/P 6) | 41 ± 1 | 34 ± 2 |
| pLL10-PEG (N/P 2) | 81 ± 1 | 54 ± 0.4 |
| pLL50-PEG (N/P 2) | 120 ± 2 | 66 ± 4 |

Values are an average ± SD (n = 3).
[a]P < 0.05 vs. polyplex diameter with model siRNA by unpaired t-test.

Cytotoxicity and Suppression of Native mRNA in Mammary MVEC by chol-siRNA Polyplexes Unlike free siRNA, free chol-siRNA is active in vitro (Lorenz et al. (2004) Bioorg. Med. Chem. Lett., 14:4975-7) and in vivo (Vinogradov et al. (1998) Bioconjug. Chem., 9:805-12). Thus, it was determined whether complexation of chol-siRNA can increase the suppression of mRNA by siRNA polyplexes. To provide a model target cell that is similar to primary cells and potentially decrease variability between studies in vitro and future studies with murine models in vivo, murine MVEC were isolated from the mammary fat pad of the Immortomouse® strain (Jat et al. (1991) Proc. Natl. Acad. Sci., 88:5096-100). The Immortomouse® strain carries a temperature-sensitive SV40 Large T antigen under the control of the H-2 Kb promoter (activated by interferon-γ [IFN-γ]), which can be used to conditionally immortalize isolated primary cells and decrease the number of primary cell isolations when grown at permissive temperature (33° C.). MVEC (Langley et al. (2003) Cancer Res., 63:2971-6) and other cell types (Takacs-Jarrett et al. (2001) Am. J. Physiol. Cell Physiol., 280:C228-36; Sweeney et al. (2001) Am. J. Physiol. Cell Physiol., 281:C1695-705) isolated from various Immortomouse® tissues have also been shown to retain the functional phenotype of the original primary cells after at least 3' passages.

Mammary MVEC were isolated from the female homozygous Immortomouse® strain by FACS, double selecting for the TNF-α induced expression of E-Selectin (CD62E) and VCAM-1 (CD106) (Langley et al. (2003) Cancer Res., 63:2971-6). IFN-γ was not added during any stage of isolation to avoid possible long term effects on mammary MVEC surface and function. A cobblestone morphology (FIG. 4A) and capillary-like structure in Matrigel™ (FIG. 4B) characteristic of vascular endothelial cells (Langley et al. (2003) Cancer Res., 63:2971-6) were observed. Cells were not used beyond passage 20 at 33° C. as a decrease in growth rate was consistently observed after this passage.

To determine whether chol-siRNA increases suppression of native mRNA, Cyclophilin B (CYPB) mRNA levels in mammary MVEC treated with polyplexes of CYPB siRNA (single siRNA or pool of 4 siRNA constructs) or chol-CYPB siRNA (same sequence as single CYPB siRNA but with 3' cholesterol on sense strand) were compared to CYPB mRNA levels in mammary MVEC treated with polyplexes containing single non-targeting siRNA (FIG. 5A). CYPB was chosen as a model of native mRNA because it is expressed at high levels and knockout does not affect cell viability (Lee et al. (2009) Biochem. Biophys. Res. Commun., 378:192-6).

Varied levels of CYPB mRNA suppression were observed with single or pooled CYPB siRNA polyplexes that did not exceed 40% (FIG. 5A), whereas single and pooled CYPB siRNA alone suppressed 88-90% CYPB mRNA by electroporation (FIG. 5B). Chol-CYPB siRNA increased suppression of CYPB mRNA by BDNG polyplexes (35%, P<0.05, n=2) and PLL10-PEG (69%, P<0.001, n=2) over equivalent CYPB siRNA polyplexes but had no statistical effect on PEI-PEG or PLL50-PEG polyplexes (FIG. 5A). In contrast, chol-CYPB siRNA alone suppressed 30% CYPB mRNA by transfection (FIG. 5A) and 10% by electroporation (FIG. 5B). Each chol-CYPB siRNA polyplex had low level cytostatic effects but little or no cytotoxicity compared to mammary MVEC alone or mammary MVEC treated with chol-CYPB siRNA under the same transfection conditions (FIG. 6). Thus, chol-siRNA increases suppression of native mRNA by select siRNA polyplexes in mammary MVEC without increasing cytotoxicity.

Herein, evidence is provided that chol-siRNA increases the suppression of native mRNA by siRNA polyplexes. Chol-siRNA increased the suppression of CYPB mRNA in conditionally immortalized mammary MVEC by PLL-PEG and BDNG siRNA polyplexes but did not change suppression by PEI-PEG siRNA polyplexes (FIG. 5A). Differences in mRNA suppression between PLL10-PEG (88% suppression) and PLL50-PEG (30% suppression) further indicate that polycationic block length is an important factor in mRNA suppression by PLL-PEG chol-siRNA polyplexes. It is also shown that chol-siRNA selectively increases nuclease protection by siRNA polyplexes. The duration and/or extent of nuclease protection was increased for BDNG and PLL-PEG chol-siRNA polyplexes, but decreased for PEI-PEG chol-siRNA polyplexes (FIG. 3).

Without being bound by theory, there are at least three possible mechanisms that may singly or collectively explain why select chol-siRNA polyplexes suppress more mRNA than siRNA polyplexes within 48 hours. A first possibility is that, unlike unmodified CYPB siRNA, chol-CYPB siRNA is active after being released from siRNA polyplexes by serum (Merkel et al. (2009) J. Control Rel., 138:148-59) or by polyanions attached to proteoglycans on the surface of mammary MVEC. This would indicate that chol-siRNA is completely released from BDNG, PEI-PEG, and PLL50-PEG chol-CYPB siRNA polyplexes which had similar levels of CYPB mRNA suppression as free chol-CYPB siRNA (30-40% suppression) (FIG. 5A). PLL10-PEG chol-siRNA polyplexes, however, suppressed more CYPB mRNA (88% suppression) than free chol-CYPB siRNA or the other chol-siRNA polyplexes (FIG. 5A) but had similar resistance to heparin displacement of chol-siRNA as BDNG and PLL50-PEG polyplexes (FIG. 2). Although the relationship between the release of chol-siRNA by heparin and release by serum or the surface of mammary MVEC has not been established, this suggests that the same amount of chol-siRNA will be released by PLL10-PEG polyplexes during transfection as the BDNG and PLL50-PEG polyplexes. Thus, a mechanism where chol-siRNA is only active after being completely released by serum or by cell surface proteoglycans seems unlikely to fully explain differences with chol-siRNA polyplexes.

A second possibility is that chol-siRNA increases the rate of polyplex uptake by mammary MVEC. Given that mRNA suppression is a kinetic phenomenon and was assessed at only a single time point, differences in the kinetics of uptake are possible.

A third possibility is that, in addition to possible differences in release and uptake of free chol-siRNA, there are differences in the release rates of chol-siRNA from polyplexes within the endosomes. Evidence was found that suggests chol-siRNA requires polymer complexation for maximal mRNA suppression within the 48 hour time frame as free chol-CYPB siRNA suppressed 30% of CYPB mRNA by transfection (FIG. 5A) and 10% by electroporation (FIG. 5B) but 88% when transfected in PLL10-PEG polyplexes (FIG. 5A). These results suggest that the 3' cholesterol moieties of chol-siRNA stick to the cell surface and limit the amount of free chol-siRNA that is endocytosed (transfection) or diffused through transient holes in the cell membrane (electroporation). In contrast, assuming chol-siRNA is not displaced by serum or at the cell surface (or, at least, not to a large extent), polyplexes can potentially limit the interaction of chol-siRNA with the cell surface and carry a greater amount of chol-siRNA into the endosomes. Endocytosed chol-siRNA, however, must be released from the polyplexes or able to interact with the endosomal membrane and/or, possibly, intracellular transporters that traffic cholesterol from the endosomes to the endoplasmic reticulum (Holtta-Vuori et al. (2006) Biochem. Soc. Trans., 34:392-4) before it can escape the endosomes. Consistent with this possibility, PLL10-PEG suppressed more mRNA than PLL50-PEG chol-siRNA polyplexes (FIG. 5) and was more accessible to nuclease activity than PLL50-PEG (FIG. 3). This suggests that chol-siRNA in PLL10-PEG polyplexes is better able to interact with and be released from the endosomes than chol-siRNA in PLL50-PEG polyplexes. Thus, increased activity by chol-CYPB siRNA polyplexes may be through a combination of released and endocytosed chol-siRNA, but is potentially the most active when endocytosed by polyplexes. These results further suggest that cationic block length is an important factor for mRNA suppression by PLL-PEG chol-siRNA polyplexes.

The duration and/or extent of nuclease protection was increased for BDNG, PLL-PEG chol-siRNA polyplexes but decreased for PEI-PEG chol-siRNA polyplexes (FIG. 3). Differences in nuclease protection by siRNA and chol-siRNA polyplexes were not due to differences in nuclease activity against model siRNA and chol-model siRNA as both were completely degraded within an hour under the same assay conditions. The most likely explanation is that chol-siRNA changes the arrangement of siRNA polyplexes which, in turn, changes in the accessibility of complexed siRNA to nuclease activity. This is supported by changes between the hydrodynamic diameters of siRNA and chol-siRNA polyplexes (Table 2) which suggest changes in the arrangement of siRNA polyplexes by chol-siRNA. Thus, interactions between 3' cholesterol moieties of complexed chol-siRNA change the arrangement of siRNA polyplexes to make siRNA less (increased protection by BDNG, PLL10-PEG, and PLL50-PEG chol-siRNA polyplexes) or more (decreased protection by PEI-PEG chol-siRNA polyplexes) accessible to nuclease activity.

For the PLL-PEG block copolymers, it is possible that chol-siRNA forms siRNA polyplexes with better defined core-shell morphologies. Thus, a better defined shell of PEG may more effectively interfere with nuclease accessibility to siRNA within the core of the polyplex. A similar formation of core-shell polyplexes is observed with complexes of cholesterol-modified polycationic polymers and DNA (Filippov et al. (2010) Langmuir 26:4999-5006). For the PEI-PEG graft copolymer, it is possible that cholsiRNA has the opposite effect and interferes with the formation of well defined core-shell morphologies, leading to decreased protection against nuclease activity. Thus, for some polymers like PLL10-PEG, chol-siRNA may form better defined core-shell polyplexes but with the added advantage of increased mRNA suppression.

Thus, the results indicate that chol-siRNA increases nuclease protection and mRNA suppression by select siRNA polyplexes. Complexation of chol-siRNA is a simple approach to improve the systemic administration of siRNA by select siRNA polyplexes through increased plasma protection and mRNA suppression at the target tissue.

EXAMPLE 2

Unmodified siRNA or siRNA modified with 3'-cholesterol was incubated with PLL10-PEG, PLL30-PEG, or PLL50-PEG at various N/P ratios (see FIG. 7A) for 30 minutes at room temperature. Polyplexes were then incubated with nuclease-inactivated murine serum at 37° C. for one or two hours and then flash-frozen in liquid $N_2$ and stored at −20° C. Soluble cholesterol was added to thawed samples in the presence or absence of heparin and resolved on a 10% polyacrylamide gel post-stained with SYBR® Gold. A flash-freeze control was run on each gel and subtracted to account for polyplex disassembly due to flash-freezing. Bands were quantified by densitometry where % siRNA displaced is the % difference between the densities of serum-displaced siRNA and the flash-freezing control normalized to heparin-displaced siRNA at each time-point. The results are presented in FIG. 7A. Two hours was the maximum time that serum nuclease activity could be inhibited with a single dose of the recombinant ribonuclease inhibitor RNAseOUT™ (Invitrogen). These data show that (i) chol-siRNA polyplexes are stable against serum displacement of complexed siRNA for at least two hours and (ii) this stability is due to the modification of siRNA with 3'-cholesterol.

In order to determine the protection afforded by complexing chol-siRNA with PLL-PEG having different PLL block lengths, chol-siRNA was incubated with polymer for 30 minutes at room temperature at the minimum N/P ratio and then incubated in the presence or absence of 90% (v/v) murine serum at 37° C. for various lengths of time. Free chol-siRNA was completely degraded within 1 hour under the same conditions. At the end of each time point, samples were treated with RNaseOUT™ and soluble cholesterol to inhibit serum nuclease activity and prevent chol-siRNA from binding to serum proteins, respectively. Remaining complexed chol-siRNA was then displaced from the polyplexes by heparin and then resolved on a 10% polyacrylamide gel post-stained with SYBR® Gold. Remaining chol-siRNA (%) was determined by densitometry where bands from serum-treated polyplexes were normalized to bands from untreated polyplexes at the same N/P ratio. The percent protection±SD (n=2) presented in FIG. 7B is an average of two independent experiments. These data show that increasing the PLL block length increases serum nuclease protection of chol-siRNA by PLL-PEG.

The ability of chol-siRNA polyplexes of PLL-PEG to suppress luciferase expression in 4T1-Luc murine breast cancer cells was also determined Briefly, 4T1-Luc cells were transfected in serum-free complete DMEM for 4 hours with chol-siRNA polyplexes containing chol-siRNA at the various N/P ratio (200 nM chol-siRNA). After 4 hours, equal volumes of complete DMEM containing 2× serum was added to each well and luciferase expression was measured at 24 hours by an IVIS® Lumina Imaging system (Caliper Life Sciences; Hopkinton, Mass.). The average radiance from cells treated with PLL-PEG-siRNA polyplexes was normalized to average radiance from untreated cells and expressed as % remaining luciferase (FIG. 8). To determine the effects on 4T1-Luc growth, the cell number and viability were measured 24 hours post-transfection by trypan blue exclusion assay on a Cellometer® Auto T4 cell counter. Trypan blue exclusion by treated cells was similar to untreated cells (~99% exclusion). These data show that increasing the PLL block length increases the suppression of mRNA in murine breast cancer cells.

Next, the ability of the polyplexes to reduce expression in vivo was assayed. 4T1-Luc cells ($1 \times 10^6$) were injected subcutaneously into the mammary fat pad of female BALB/c and grown until between 0.5 and 0.7 cm$^3$. Vehicle alone (HEPES/NaCl, 100 µL), nuclease-resistant chol-siRNA alone, or chol-siRNA complexed with PLL-PEG was then intravenously injected at 2.5 mg chol-siRNA/kg daily on days 0, 1, and 2. The average radiance from 4T1 tumors was normalized to average radiance on day 0 within the same cohort and expressed as % luminescence±propagated SEM. The data presented in FIG. 9 show that vehicle alone, LUC chol-siRNA alone, and control chol-siRNA polyplexes were unable to suppress expression of luciferase. However, in complete contrast, LUC chol-siRNA polyplexes of PLL30-PEG and PLL50-PEG (but not PLL10-PEG) suppressed high levels of luciferase expression in primary 4T1 tumors. FIG. 10 presents images of the luminescence observed from the mice at either day 0 or day 2.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A complex comprising:
   a) a short nucleic acid molecule linked to a hydrophobic moiety, wherein said short nucleic acid molecule comprises less than about 50 nucleotides, wherein said short nucleic acid molecule is an siRNA molecule, wherein said hydrophobic moiety is cholesterol; and
   b) a linear block copolymer consisting of at least one cationically charged polymeric segment and at least one hydrophilic polymeric segment, wherein said cationically charged polymeric segment consists of about 30 to about 50 lysines, wherein said hydrophilic polymeric segment comprises poly(ethylene oxide).

2. The complex of claim 1, wherein said cationically charged polymeric segment consists of about 30 lysines.

3. The complex of claim 1, wherein said hydrophobic moiety is linked to the 3' end of the sense strand of the siRNA molecule.

4. The complex of claim 1, wherein said hydrophobic moiety is linked directly to the nucleic acid molecule or linked via a linker.

5. The complex of claim 1, further comprising at least one therapeutic agent or detectable agent.

6. A composition comprising at least one complex of claim 1 and at least one pharmaceutically acceptable carrier.

7. The composition of claim 6, further comprising at least one therapeutic agent or detectable agent.

8. A complex comprising:
a) a short nucleic acid molecule linked to a hydrophobic moiety, wherein said short nucleic acid molecule comprises less than about 50 nucleotides, wherein said short nucleic acid molecule is an siRNA molecule, wherein said hydrophobic moiety is cholesterol; and
b) a linear block copolymer consisting of at least one cationically charged polymeric segment, at least one hydrophilic polymeric segment, and a targeting ligand, wherein said cationically charged polymeric segment consists of about 30 to about 50 lysines, wherein said hydrophilic polymeric segment comprises poly(ethylene oxide).

9. A method of delivering a nucleic acid molecule to a cell, said method comprising contacting the cell with the complex of claim 1.

10. The method of claim 9, wherein said method comprises administering said complex to a subject.

11. The method of claim 10, wherein said complex is administered intravenously.

12. A method of inhibiting the expression of a protein in a cell, said method comprising contacting the cell with the complex of claim 1.

13. The method of claim 12, wherein said method comprises administering said complex to a subject.

14. The method of claim 13, wherein said complex is administered intravenously.

15. A method of inhibiting a disease or disorder in a subject, said method comprising administering at least one composition of claim 6 to said subject.

* * * * *